(12) United States Patent
Shen et al.

(10) Patent No.: US 11,262,365 B2
(45) Date of Patent: Mar. 1, 2022

(54) KIT FOR HEMOGLOBIN A1C QUANTITATIVE ANALYSIS

(71) Applicant: I-SENS, INC., Seoul (KR)

(72) Inventors: Dongxuan Shen, Gyeonggi-do (KR); Jihoon Kim, Seoul (KR); Joo Young Cho, Incheon (KR); Kap Soo Park, Gyeonggi-do (KR); Hyeong Eun Kim, Incheon (KR); Hyun Kyu Cho, Gyeonggi-do (KR); Seok Won Lee, Gyeonggi-do (KR); Hakhyun Nam, Seoul (KR); Geun Sig Cha, Seoul (KR)

(73) Assignee: I-SENS, INC., Seoul (KR)

( * ) Notice: Subject to any disclaimer, the term of this patent is extended or adjusted under 35 U.S.C. 154(b) by 562 days.

(21) Appl. No.: 16/340,833

(22) PCT Filed: Aug. 10, 2017

(86) PCT No.: PCT/KR2017/008700
§ 371 (c)(1),
(2) Date: Apr. 10, 2019

(87) PCT Pub. No.: WO2018/070652
PCT Pub. Date: Apr. 19, 2018

(65) Prior Publication Data
US 2019/0242910 A1 Aug. 8, 2019

(30) Foreign Application Priority Data
Oct. 12, 2016 (KR) .................. 10-2016-0131863

(51) Int. Cl.
*G01N 33/72* (2006.01)
*C12Q 1/37* (2006.01)
(Continued)

(52) U.S. Cl.
CPC ......... *G01N 33/721* (2013.01); *C07K 14/805* (2013.01); *C12N 9/0022* (2013.01);
(Continued)

(58) Field of Classification Search
CPC ................. G01N 33/721; G01N 33/72; G01N 2333/9065; G01N 2400/10;
(Continued)

(56) References Cited

U.S. PATENT DOCUMENTS

2007/0224685 A1* 9/2007 Kouzuma ................ C12N 9/96
436/66

FOREIGN PATENT DOCUMENTS

JP 2001215229 A 8/2001
JP 2009034110 A 2/2009
(Continued)

OTHER PUBLICATIONS

PCT International Search Report dated Nov. 20, 2017 for International Application No. PCT/KR2017/008700, from which the instant application is based, 3 pgs.

*Primary Examiner* — Jennifer Wecker
*Assistant Examiner* — Michael Paul Shimek
(74) *Attorney, Agent, or Firm* — Fredrikson & Byron, P.A.

(57) ABSTRACT

The present invention relates to a kit for quantitative analysis of glycated hemoglobin (HbA1c), and the kit for quantitative analysis of HbA1c according to the present invention has excellent long-term stability of an enzyme reagent and thus has an effect of easily overcoming the disadvantages of the conventional reagents used in enzyme assays (e.g., storage, accuracy, portability, convenience of use, etc.).

18 Claims, 26 Drawing Sheets

(51) Int. Cl.
   *C07K 14/805* (2006.01)
   *C12N 9/06* (2006.01)
   *C12Q 1/28* (2006.01)

(52) U.S. Cl.
   CPC .............. *C12N 9/0032* (2013.01); *C12Q 1/28* (2013.01); *C12Q 1/37* (2013.01); *G01N 33/72* (2013.01); *C12Y 105/03* (2013.01); *G01N 2333/9065* (2013.01); *G01N 2400/10* (2013.01); *G01N 2800/22* (2013.01)

(58) Field of Classification Search
   CPC .............. G01N 2800/22; C07K 14/805; C12N 9/0022; C12N 9/0032; C12Q 1/28; C12Q 1/37; C12Y 105/03
   See application file for complete search history.

(56) References Cited

FOREIGN PATENT DOCUMENTS

| | | |
|---|---|---|
| KR | 101207418 B1 | 12/2012 |
| KR | 1020130119742 A | 11/2013 |
| KR | 101723025 B1 | 4/2017 |
| WO | 2002021142 A1 | 3/2002 |

\* cited by examiner

[Figure 1]
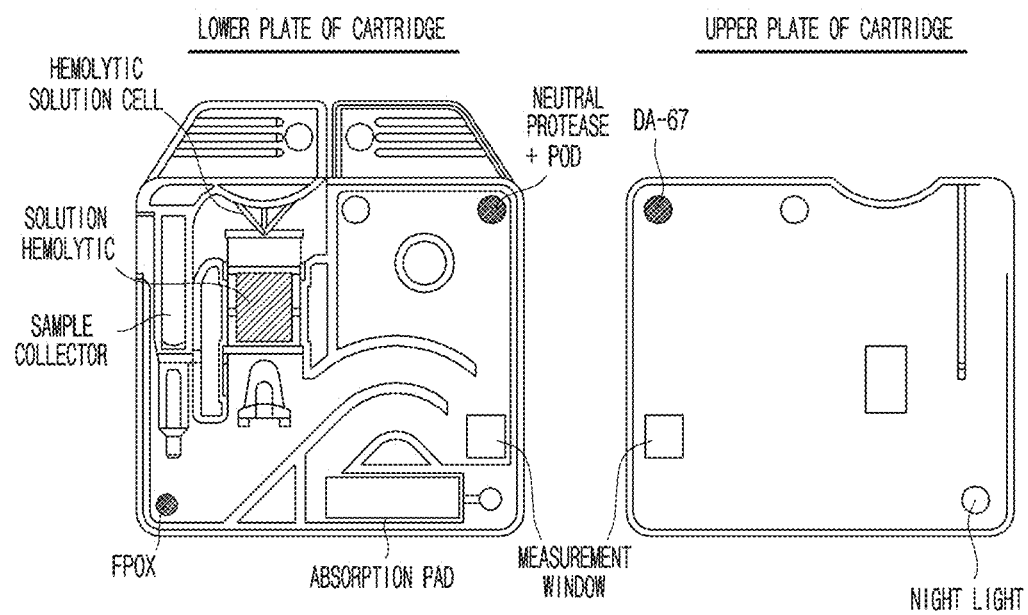

[Figure 2]
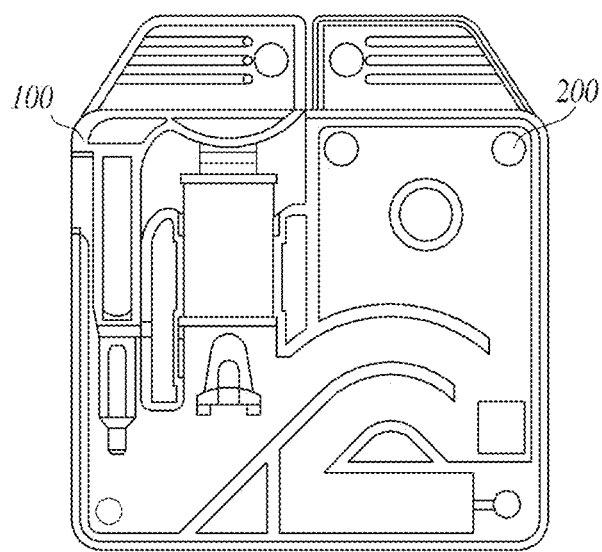

[Figure 3]
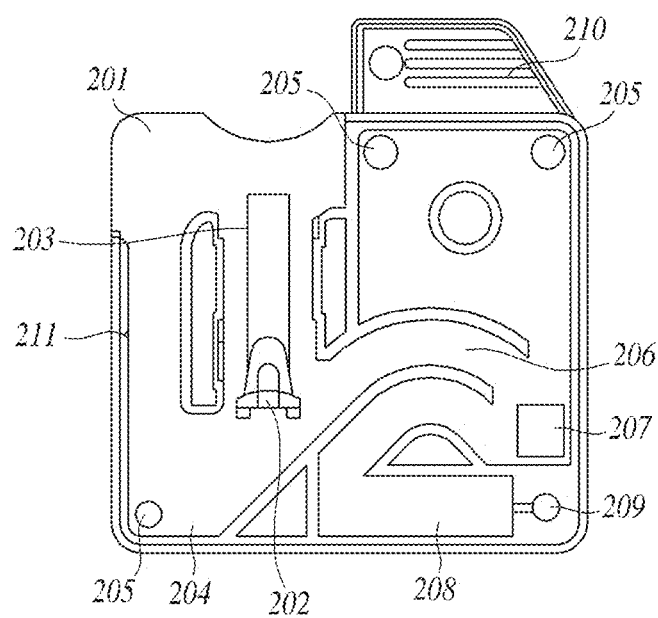

[Figure 4]
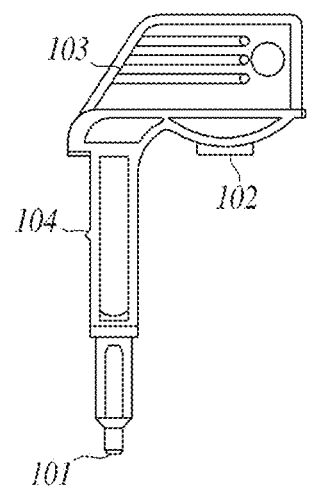

[Figure 5]
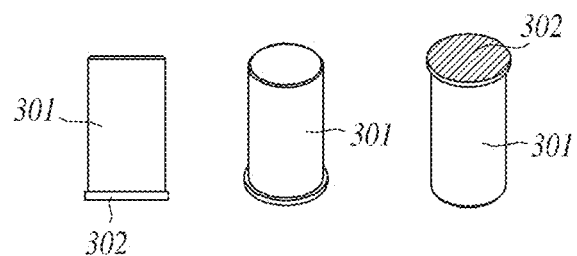

[Figure 6]
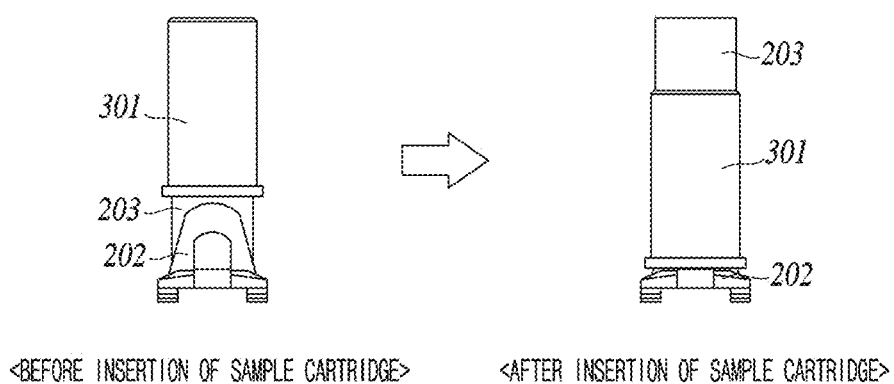

[Figure 7]
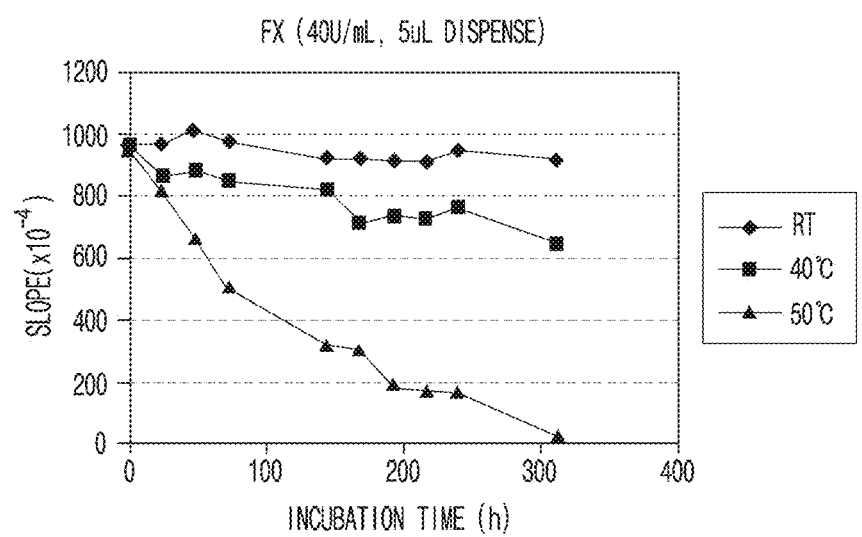

[Figure 8]
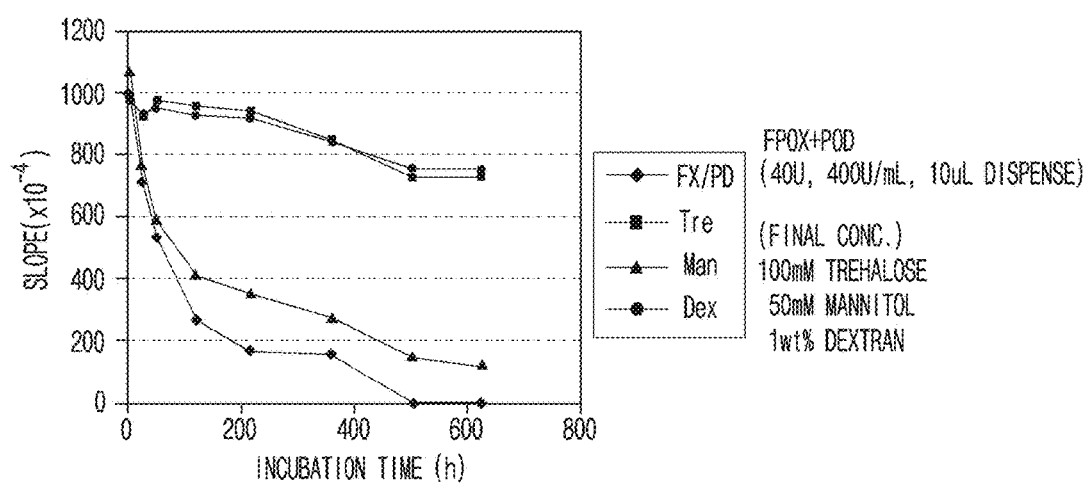

[Figure 9]
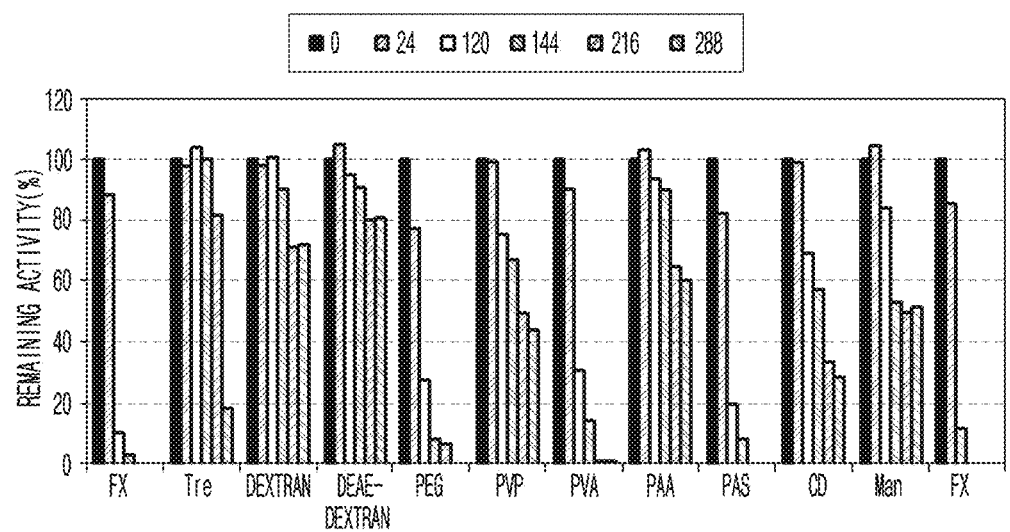

[Figure 10]
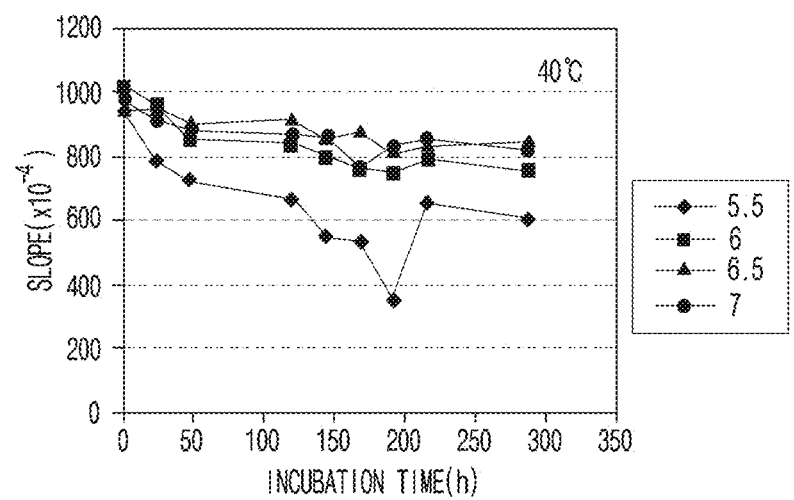

[Figure 11]
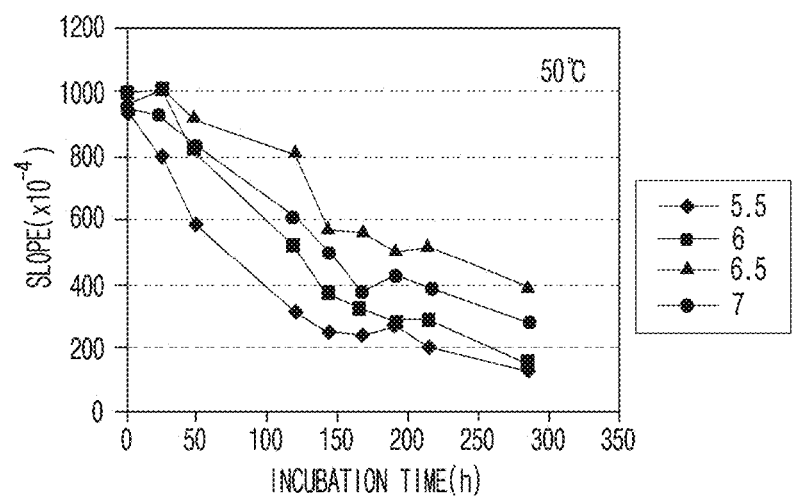

[Figure 12]
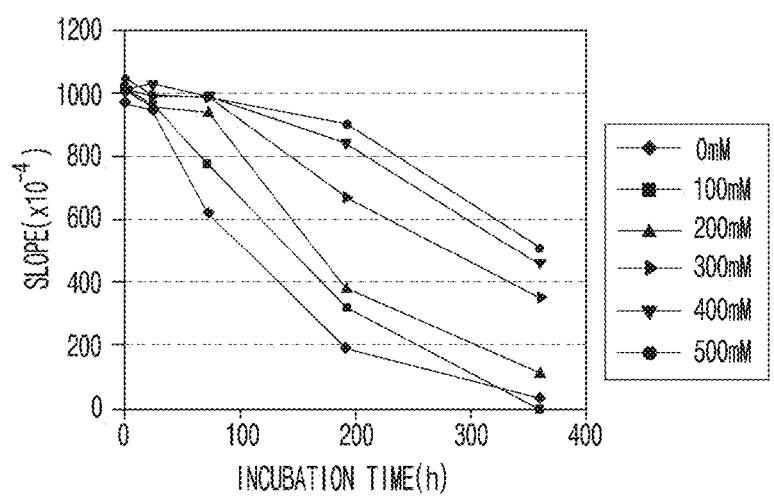

[Figure 13]
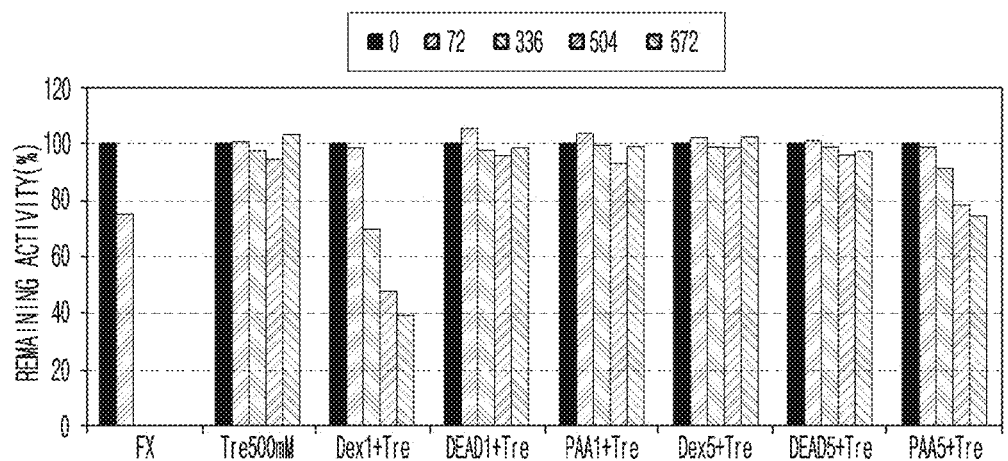

[Figure 14]
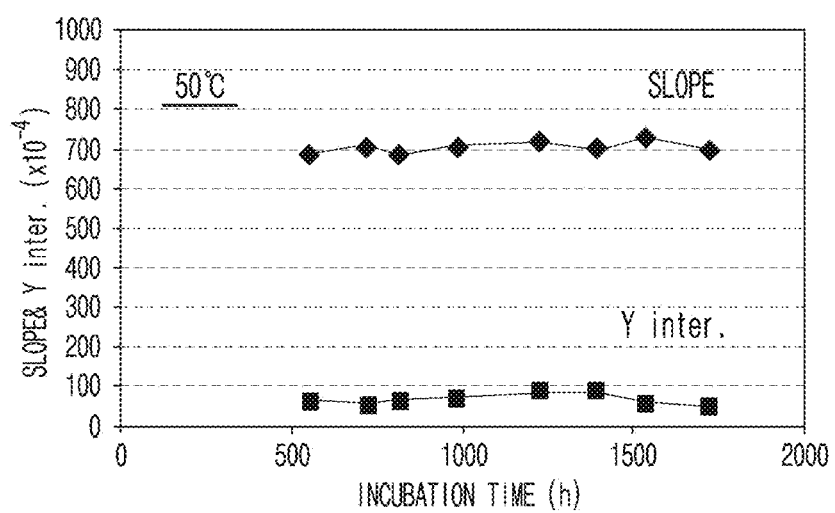

[Figure 15]
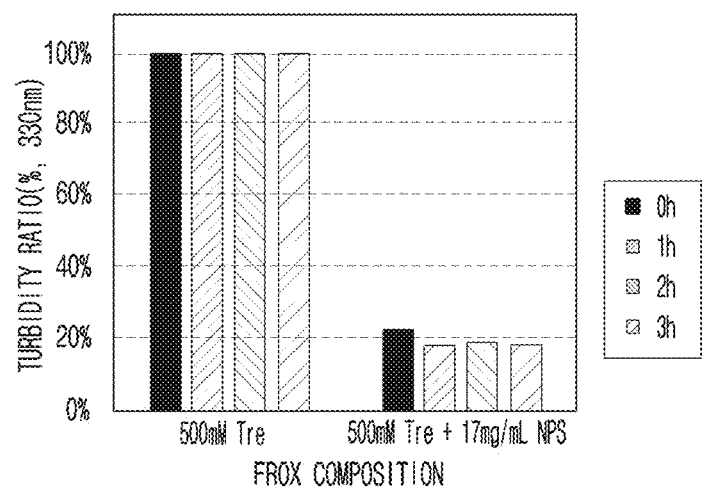

[Figure 16]
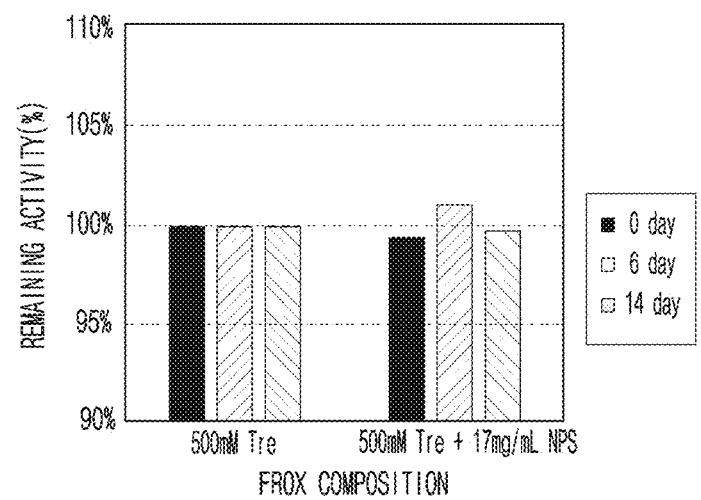

[Figure 17]
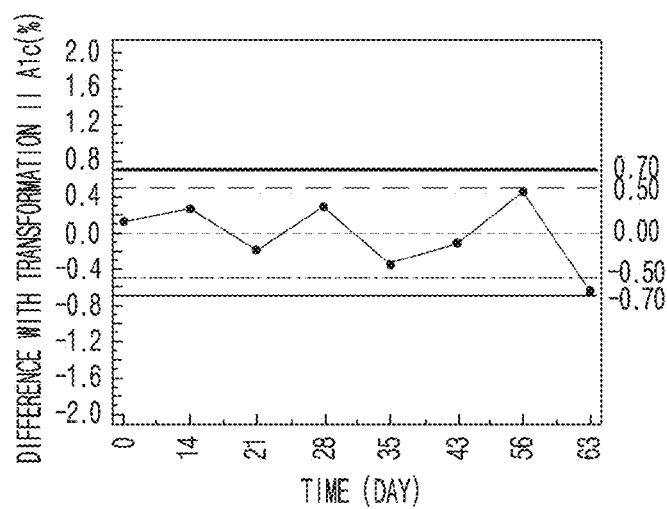

[Figure 18]
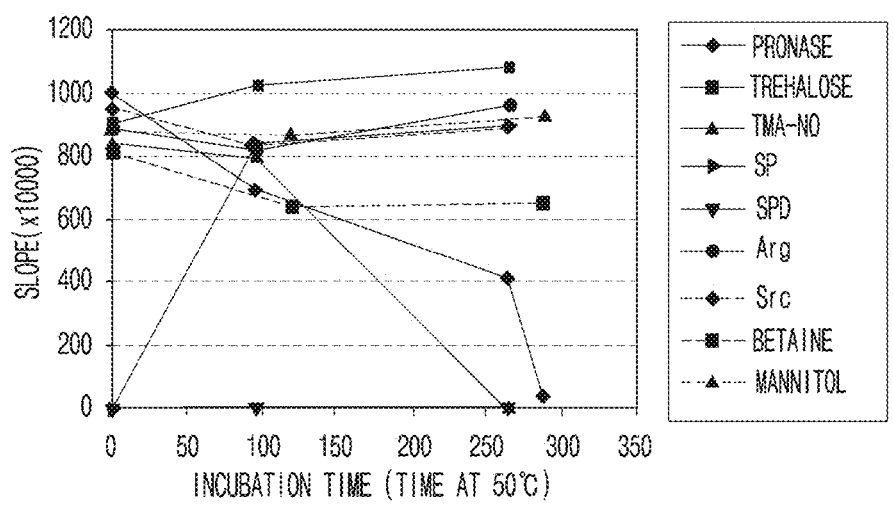

[Figure 19]
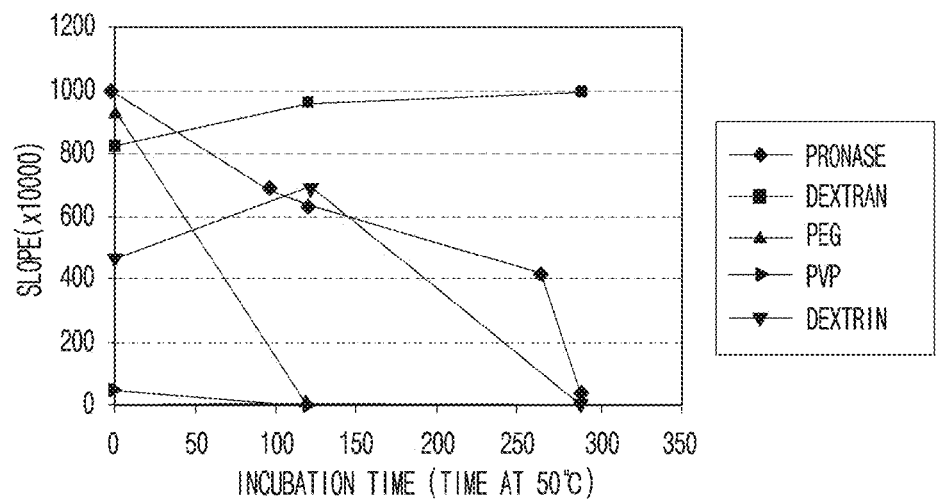

[Figure 20]
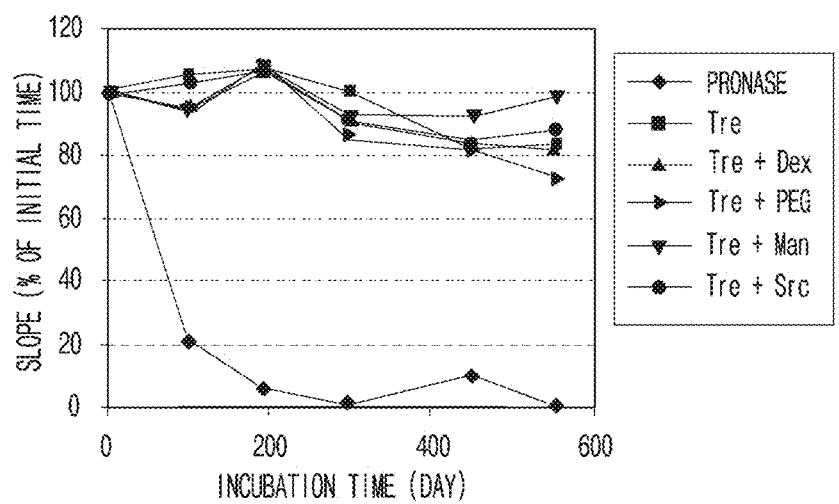

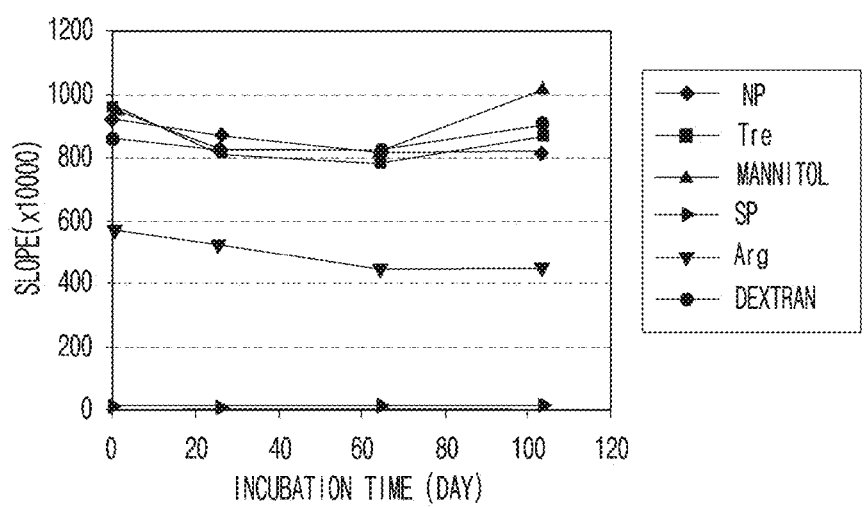
[Figure 21]

[Figure 22]
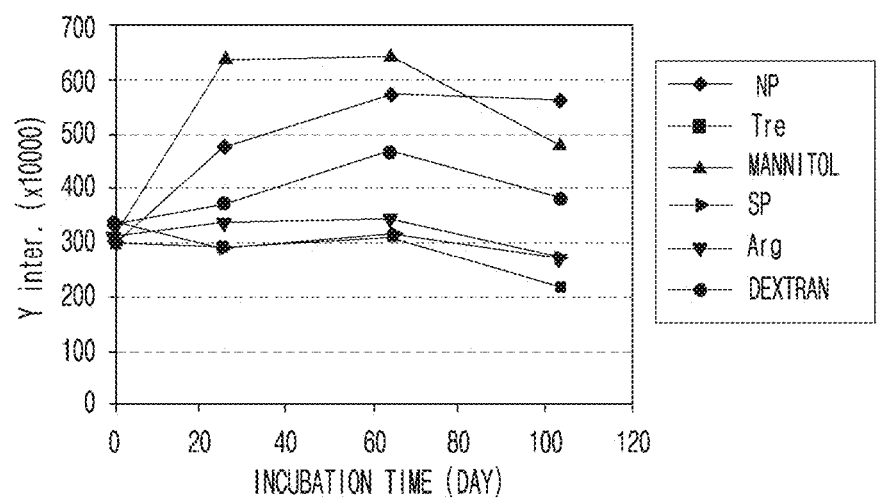

[Figure 23]
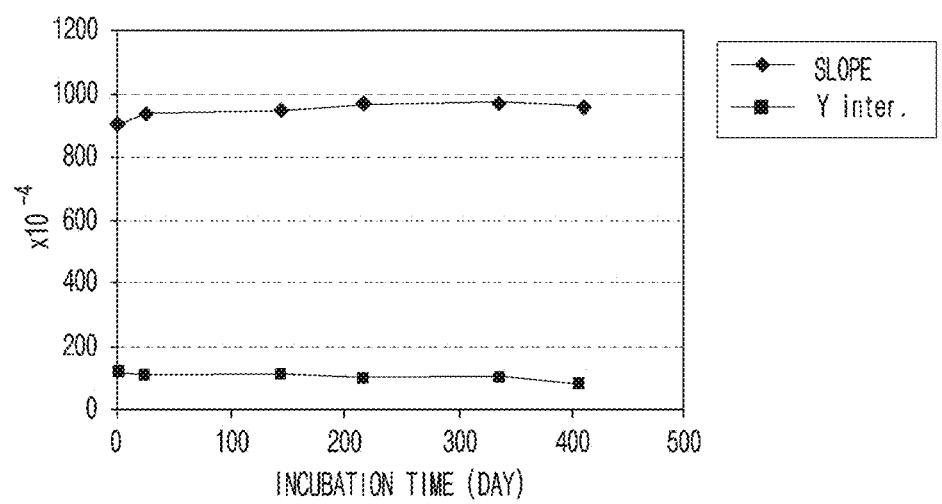

[Figure 24]
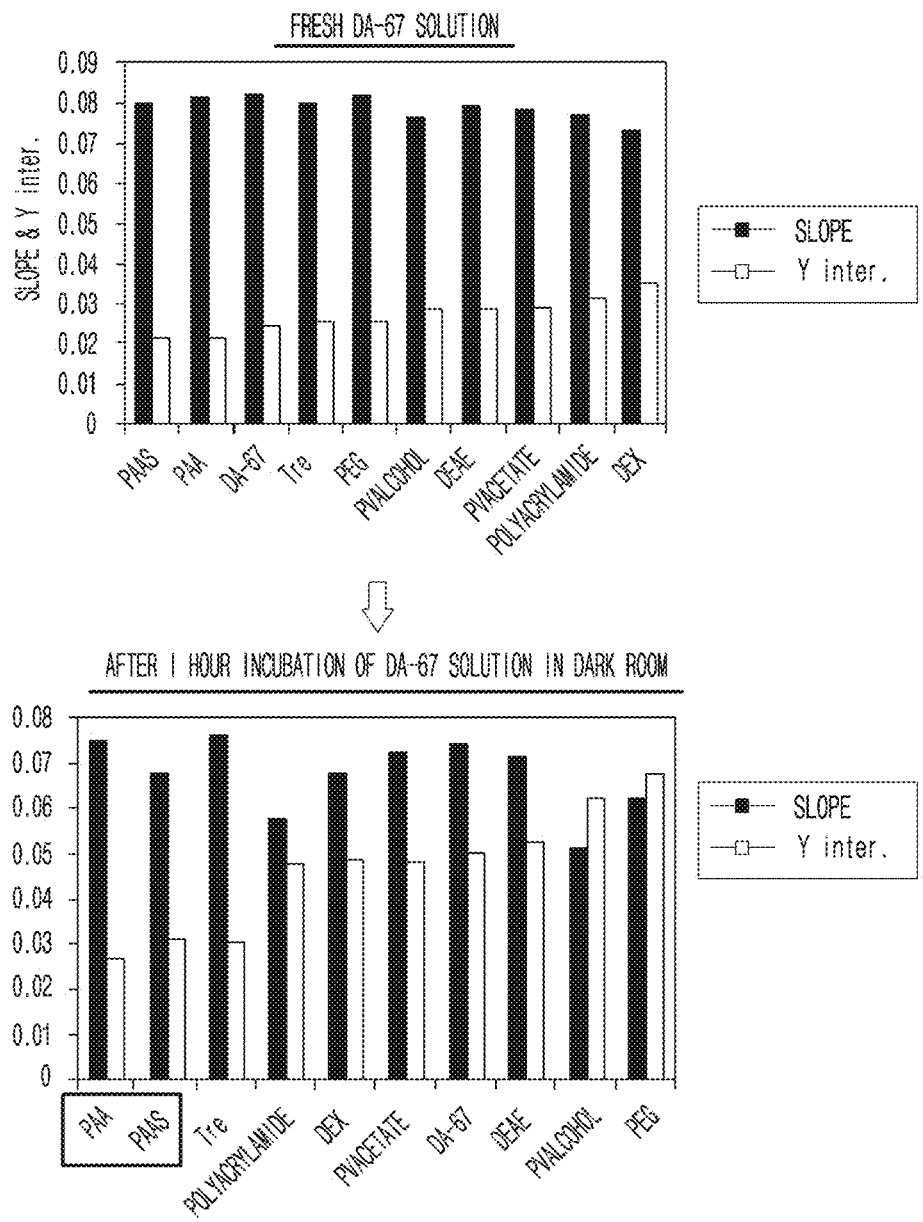

[Figure 25]
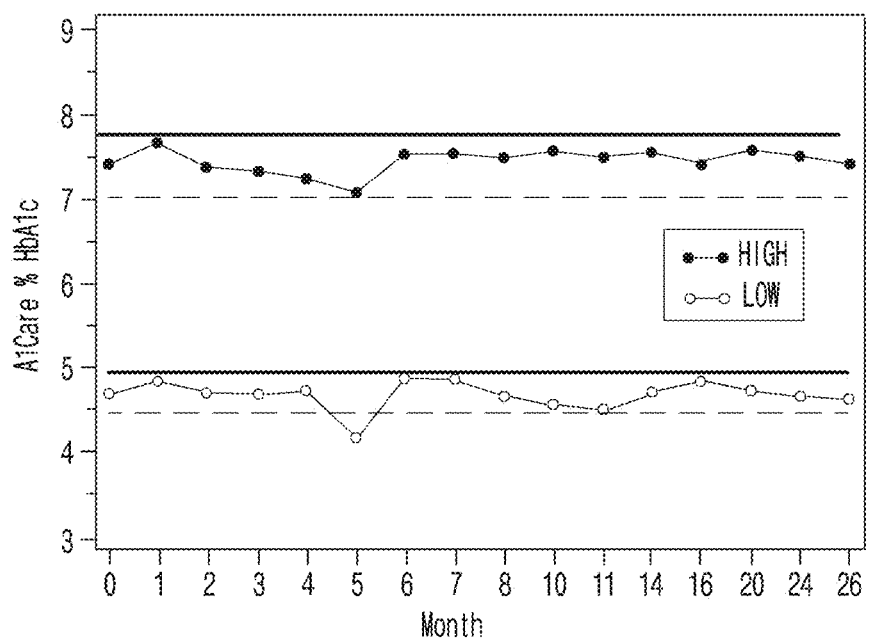

[Figure 26]
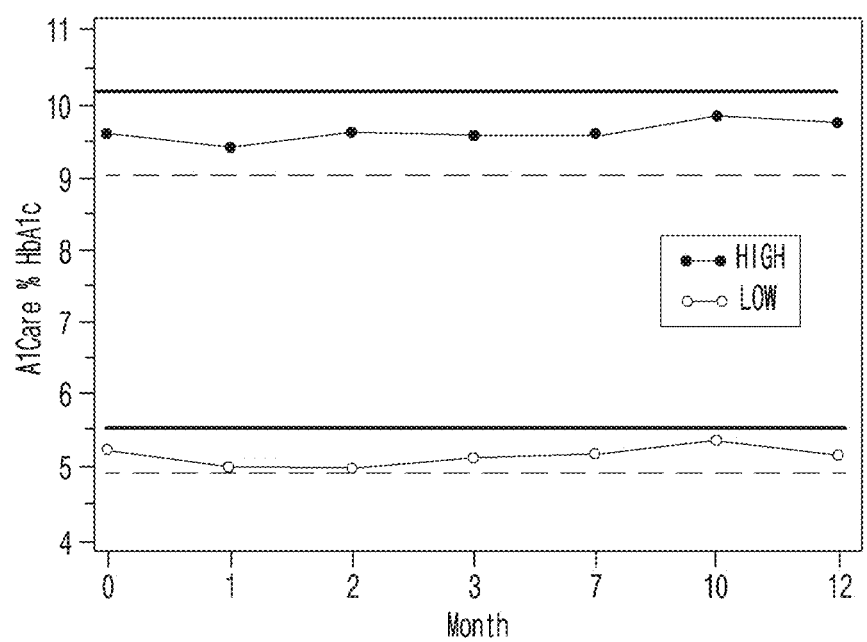

//KIT FOR HEMOGLOBIN A1C QUANTITATIVE ANALYSIS

RELATED APPLICATIONS

This application is a 35 U.S.C. 371 national stage filing from International Application No. PCT/KR2017/008700, filed Aug. 10, 2017, which claims priority to Korean Application No. 10-2016-0131863, filed Oct. 12, 2016, the teachings of which are incorporated herein by reference.

TECHNICAL FIELD

The present disclosure relates to a kit for quantitative analysis of glycated hemoglobin.

BACKGROUND ART

Currently, in the medical diagnosis field, for the detection and quantification of specific samples contained in biological samples (e.g., blood, serum, urine, cell sap, etc.), various analytical techniques (e.g., enzyme assay, immunoassay, chemical colorimetric assay, electrochemical assay, fluorescence labeling and measurement, chemiluminescent labeling and measurement, etc.) are used. These analytical techniques are applied and used in large equipments (e.g., automatic assay devices used in clinical test centers of large hospitals) or point-of-care testing (hereinafter, POCT) devices employing platforms (e.g., test strips, cartridges, etc.).

While the use of large equipments has advantages in that it is possible to handle a large quantity of samples and the measured values are highly reliable, it has a disadvantage in that the place of use is limited because these equipments are large and complex due to the nature of mechanical equipments and thus can be used in special examination rooms. Additionally, these equipments frequently require a pretreatment process and are cumbersome in terms of maintenance and management because various kinds of reagents and sensors must be used with periodic replacement, respectively.

Meanwhile, in the case of a POCT, the reliability of measured values is lower than that of large equipments. However, it has advantages in that the place of use is not limited and the measurement can be performed quickly and is thus widely used in the field of medical diagnosis. In particular, unlike large equipments in which various kinds of reagents and sensors must be provided and installed, respectively, a cartridge-type POCT is configured such that a unit for supplying biological samples, a reaction reagent, and a detection area are constituted in one cartridge and thus provides user convenience at the time of measurement. In addition, the POCT has an advantage in that the risk of contamination by exposure to biological samples after measurement is low and thus has a merit in terms of safety.

Meanwhile, in the diagnosis of diabetes, there is a growing need for the POCT of glycated hemoglobin as well as measurement of blood glucose levels. Glycated hemoglobin (hereinafter, HbA1c) refers to a hemoglobin bound to glucose. The measurement of HbA1c contained in blood not only provides average blood glucose levels of a patient for the past 3 to 4 months regardless of presence/absence of meals and the physical state of the patient but also serves as an index to evaluate the efficiency of the measurement of blood glucose levels carried out by the patient, thus drawing much public attention.

In 2010, the American Diabetes Association provided a HbA1c value of 6.5% or higher as the criterion to diagnose diabetes and also explicitly specified that the HbA1c value should be measured by an approved test. Additionally, in 2011, the World Health Organization (WHO) reported that the measurement of HbA1c had been used simply for monitoring diabetic patients, but, from then on, HbA1c measurement could be used to diagnose diabetes based on strict quality assurance and standardized methods. In fact, many cartridge-type POCT devices for measurement of HbA1c contained in the blood have been reported and released. For example, KR Patent Application No. 10-2012-0013841 discloses a hemolytic reagent composition capable of performing quantitative analysis of HbA1c using an enzymatic method.

However, all existing commercially available enzyme assay reagents for the measurement of HbA1c are manufactured and sold as solutions, and have limitations on long-term stability, storage, accuracy, portability, convenience of use, etc. For example, among the enzyme assay reagents for measurement, fructosyl peptide oxidase (FPOX) is known to have poor thermal stability and the activity is significantly decreased with time at room temperature.

As such, the present inventors have made efforts to secure the long-term stability of enzyme reagents used for the method of enzyme assay measurement among the methods for measuring HbA1c, and improve durability and accuracy of a kit for quantitative analysis of HbA1c. As a result, they have confirmed that the kit for quantitative analysis of HbA1c according to the present invention has excellent long-term stability of an enzyme reagent and thus the disadvantages of the conventional reagents used in enzyme assays (e.g., storage, accuracy, portability, convenience of use, etc.) can be easily overcome thereby completing the present invention.

DISCLOSURE OF THE INVENTION

Technical Problem

One object of the present invention is to provide a kit for quantitative analysis of HbA1c which contains a sample with improved long-term stability.

Technical Solution

In order to achieve the objects, the present invention provides a kit for quantitative analysis of glycated hemoglobin (HbA1c), which contains:

a first composition containing a saccharide and a nitrite compound;

a second composition containing at least one selected from the group consisting of a saccharide, an amino acid, a sugar alcohol, and a polyamine; a proteolytic enzyme; and an oxidizing agent;

a third composition containing at least one kind selected from the group consisting of a saccharide and an organic polymer; and a fructosyl amino acid oxidase (FAOD); and a fourth composition containing saccharides and a color developing reagent.

Advantageous Effects

The kit for quantitative analysis of HbA1c according to the present invention has excellent long-term stability of an enzyme reagent and thus has an effect of easily overcoming the disadvantages of the conventional reagents used in enzyme assays (e.g., storage, accuracy, portability, convenience of use, etc.).

BRIEF DESCRIPTION OF THE DRAWINGS

FIG. 1 shows an embodiment of a specific structure of a kit for quantitative analysis of HbA1c according to the present invention.

FIG. 2 shows an embodiment of a specific frontal perspective view of a kit for quantitative analysis of HbA1c according to the present invention.

FIG. 3 shows an embodiment of a front perspective view showing a reaction cartridge in a kit for quantitative analysis of HbA1c according to the present invention.

FIG. 4 is an image showing a chamber for storing reaction solution provided in a kit for quantitative analysis of HbA1c according to the present invention.

FIG. 5 is an image showing an insertion-type sample cartridge in a kit for quantitative analysis of HbA1c according to the present invention.

FIG. 6 is an image, in a kit for quantitative analysis of HbA1c according to the present invention, showing that a chamber for storing reaction solution 301 moves toward a covertape breaking unit 202 while simultaneously an insertion-type sample cartridge 100 is inserted into a reaction cartridge 200, and as a result, the reaction solution is released from a chamber for storing the reaction solution 301 and moves to a mixing unit 204.

FIG. 7 is a graph showing the evaluation results of thermal stability of fructosyl peptide oxidase (FPOX) reagent with time.

In the above graph, the slope represents activity.

FIG. 8 is a graph showing the evaluation results of thermal stability with time of a mixture of FPOX and peroxidase (POD) reagents, after trehalose, mannitol, or dextran is added thereto.

FIG. 9 is a graph showing the evaluation results of thermal stability with time of a mixture of FPOX and POD reagents, after adding various kinds of stabilizers thereto.

In the above graph, the unit of the number shown at the top of FIG. 9 represents minute (min); Tre represents trehalose, PEG represents poly ethylene glycol, PVP represents polyvinylpyrrolidone, PVA represents polyvinyl alcohol, PAA represents polyacryl acid, PAS represents paraaminosalicylic acid, and Man represents mannitol.

FIG. 10 is a graph showing the evaluation results of thermal stability with time of FPOX at 40° C., after adding various kinds of buffers with various pH values thereto.

In the above graph, the values on the right represent each pH value.

FIG. 11 is a graph showing the evaluation results of thermal stability with time of FPOX at 50° C., after adding various kinds of buffers with various pH values thereto.

In the above graph, the values on the right represent each pH value.

FIG. 12 is a graph showing the evaluation results of thermal stability of FPOX observed when trehalose at various concentrations is added to FPOX.

FIG. 13 is a graph showing the evaluation results of thermal stability of FPOX observed when trehalose was treated alone or by mixing with other kinds of stabilizers.

FIG. 14 is a graph showing the evaluation results of thermal stability of FPOX with time after trehalose and buffer are added to FPOX.

In the above graph, slope represents activity and Inter (Y Intercept) represents the background absorbance of the measurement system itself (the absorbance value in the absence of a sample).

FIG. 15 is a graph showing the evaluation results of turbidity of a solution when FPOX was treated with trehalose alone or additionally by mixing with Neo Protein Saver, which is known as a protein stabilizer.

FIG. 16 is a graph showing the comparative evaluation results of thermal stability possessed by a reagent composition between a case where FPOX was treated with trehalose alone and a case where FPOX is additionally mixed with Neo Protein Saver.

FIG. 17 is a graph showing the evaluation results of thermal stability possessed by a reagent composition consisting of FPOX, trehalose, Neo Protein Savor (NPS), and buffer (100 mM phosphate buffer, pH 6.5).

FIG. 18 is a graph showing the evaluation results of thermal stability of pronase with time when pronase was treated with various kinds of low molecular weight stabilizers.

FIG. 19 is a graph showing the evaluation results of thermal stability of pronase with time when pronase was treated with various kinds of high molecular weight stabilizers.

FIG. 20 is a graph showing the evaluation results of thermal stability of pronase with time when pronase was treated with trehalose and various kinds of high molecular weight molecules as stabilizers.

FIG. 21 is a graph showing the evaluation results of thermal stability of pronase with time when neutral pronase was treated with various kinds of stabilizers. In particular, NP represents neutral protease, Tre represents trehalose, SP represents Spermine, Arg represents arginine.

FIG. 22 is a graph showing the background observed when neutral protease was treated with various kinds of stabilizers.

FIG. 23 is a graph showing the results of performance observed with time when $NaNO_2$ was treated with MES buffer, D10, and trehalose.

FIG. 24 is a graph showing the results of changes in performance observed after DA-67 was treated with various kinds of stabilizers.

FIG. 25 is a graph showing the evaluation results of stability of a kit for quantitative analysis of HbA1c according to the present invention after storing the kit in a refrigerator.

FIG. 26 is a graph showing the evaluation results of stability of a kit for quantitative analysis of HbA1c according to the present invention after storing the kit at room temperature.

MODE FOR CARRYING OUT THE INVENTION

Hereinafter, the present invention will be described in detail.

The present invention provides a kit for quantitative analysis of HbA1c, which contains:

a first composition containing a saccharide and a nitrite compound;

a second composition containing at least one selected from the group consisting of a saccharide, an amino acid, a sugar alcohol, and a polyamine; a proteolytic enzyme; and an oxidizing agent;

a third composition containing at least one kind selected from the group consisting of a saccharide and an organic polymer; and a fructosyl amino acid oxidase (FAOD); and a fourth composition containing saccharides and a color developing reagent.

In particular, the second composition may contain a secondary first composition comprising at least one selected from the group consisting of a saccharide, an amino acid, a sugar alcohol, and a polyamine; and a proteolytic enzyme; and a secondary second composition comprising at least one selected from the group consisting of a saccharide, an amino acid, a sugar alcohol, and a polyamine; and an oxidizing agent.

Additionally, in the above invention, a combination of two selected from each composition may be mixed with each other, and the combination of two may be a combination between a second composition and a third composition.

In particular, the saccharide may be at least one selected from the group consisting of a monosaccharide, a disaccharide, and a polysaccharide, and more specifically, the monosaccharide may be fructose, galactose, glucose, or mannose;

the disaccharide may be sucrose, lactose, maltose, trehalose, turanose, or cellobiose; and the polysaccharide may be dextran, diethylamino ethyl-dextran, dextrin, cellulose, or β-glucans.

Additionally, as the amino acid, at least one selected from the group consisting of arginine, sarcosine, alanine, cysteine, aspartic acid, glutamic acid, phenylalanine, glycine, histidine, isoleucine, lysine, leucine, methionine, asparagine, pyrrolysine, proline, glutamine, serine, and threonine may be used.

Furthermore, as the sugar alcohol, at least one selected from the group consisting of mannitol, xylitol, sorbitol, maltitol, an erythritol may be used.

Additionally, as the polyamine, at least one selected from the group consisting of spermine, putrescine, spermidine, cadaverine, agmatine, and ornithine may be used.

Furthermore, as the organic polymer, at least one selected from the group consisting of polydiene-based, polyalkene-based, polyacrylic acid-based, polyacrylate-based, polyacrylamide-based, polymethacrylic acid-based, polymethacrylate-based, polymethacrylamide-based, polyvinyl ether-based, polyvinyl thioether-based, polyvinyl alcohol-based, polyvinyl ketone-based, polyvinyl halide-based, polyvinyl nitrile-based, polyvinyl ester-based, polystyrene-based, polyphenylene-based, polyoxide-based, polycarbonate-based, polyester-based, polyanhydride-based, polyurethane-based, polysulfonate-based, nitroso-polymer-based, polysiloxane-based, polysulfide-based, polythioester-based, polysulfone-based, polysulfonamide-based, polyamide-based, polyimine-based, polyurea-based, polyaniline-based, polythiophene-based, polypyrrole-based, polyheterocyclic, polyether-based, polyphosphate-based, and polysilsesquioxane-based homopolymers; a derivative thereof; and a copolymer thereof or a derivative thereof may be used.

Additionally, as the nitrite compound, at least one selected from the group consisting of sodium nitrite, potassium nitrite, magnesium nitrite, and calcium nitrite may be used.

In particular, it is preferred that the nitrite compound be added at a concentration of 1 mM to 500 mM. When the nitrite compound is lower than 1 mM, there is a problem in that the protein structure of hemoglobin cannot be smoothly modified, whereas when the nitrite compound exceeds 500 mM, there is a problem in that scattering occurs at the time of measurement of the total hemoglobin concentration.

Furthermore, as the proteolytic enzyme, at least one selected from the group consisting of pronase, protease A, protease N, dispase, neutral protease, glu-C, papain, trypsin, and pepsin may be used.

In particular, it is preferred that the proteolytic enzyme be added in an amount of 500 U/mL to 1000 U/mL. When the proteolytic enzyme is added less than 500 U/mL, there is a problem in that the sensitivity of the overall reaction becomes reduced, whereas when the proteolytic enzyme is added greater than 500 U/mL, there is a problem in that the enzyme used together is also decomposed together and thus the reactivity is deteriorated.

Additionally, the oxidizing agent may be used without limitation as long as it oxidizes the hydrogen peroxide produced by FAOD, for example, peroxidase (POD) may be used.

In particular, it is preferred that the oxidizing agent be added in an amount of 5 U/mL to 900 U/mL. When the oxidizing agent is added less than 5 U/mL, there is a problem in that the sensitivity of the overall reaction becomes reduced, whereas when the oxidizing agent is added greater than 900 U/mL, there is a problem in that the color possessed by the enzyme itself is similar to that of hemoglobin and becomes an obstacle to the measurement of HbA1c concentration.

Furthermore, it is preferred that the fructosyl amino acid oxidase (FAOD) be fructosyl peptide oxidase (FPOX).

In particular, it is preferred that the FAOD be added in an amount of 1.0 U/mL to 300 U/mL. When the FAOD is added less than 1.0 U/mL, there is a problem in that the sensitivity of the overall reaction becomes reduced, whereas when the FAOD is added greater than 300 U/mL, there is a problem in that FAOD is used excessively more than necessary thus being uneconomical.

Additionally, as the color developing reagent, at least one selected from the group consisting of N-(carboxymethylaminocarbonyl)-4,4'-bis(dimethylamino)diphenylamine (DA-64; Wako Pure Chemical Industries Ltd.), 10-(carboxymethylaminocarbonyl)-3,7-bis(dimethylamino)phenothiazine sodium salt (DA-67: Wako Pure Chemical Industries Ltd.), 10-(N-methylcarbamoyl)-3,7-bis(dimethylamino)-1H-phenothiazine (MCDP: product of Dojindo Laboratories), N,N,N',N',N'',N''-hexa-3-sulfopropyl-4,4',4''-triaminotriphenylmethane (TPM-PS: product of Dojindo Laboratories), and ortho-phenylenediamine (OPD) may be used.

In particular, it is preferred that the color developing reagent be added at a concentration of 5 mg/dL to 100 mg/dL. When the color developing reagent is added less than 5 mg/dL, there is a problem in that the amount may not be sufficient to induce color development, whereas when the color developing reagent is added greater than 100 mg/dL, there is a problem in that spontaneous color change occurs and thereby causes an error in spectroscopic measurement. The color developing reagent is an unstable material that volatilizes spontaneously due to external or temperature when used alone, and thus caution is required in use.

The kit for quantitative analysis of HbA1c according to the present invention may include a plurality of sample introduction units, and it is preferred that the first composition, second composition, third composition, and fourth composition each be independently fixed to a plurality of sample introduction units. In particular, it is preferred that the first composition, second composition, third composition, and fourth composition be fixed to the sample introduction units in a dried state.

In an embodiment, the kit for quantitative analysis of HbA1c according to the present invention may be a cartridge having a structure as follows:

in a cartridge for quantitative analysis of HbA1c including an insertion-type sample cartridge for supplying a sample and a reaction cartridge capable of receiving the insertion-type sample cartridge, the reaction cartridge includes:

a receiving unit into which the insertion-type sample cartridge is inserted to be received;

a chamber for storing reaction solution, which while being provided within the receiving unit and including an opening unit at one end, stores a reaction solution that can react with a sample inside thereof, includes a covertape which is attached to the opening unit so as to prevent the release of the stored reaction solution, and the opening unit attached to the covertape is provided to face toward the inside of the reaction cartridge;

a covertape breaking unit, which, while being provided to face the covertape of the chamber for storing reaction solution, is provided to be spaced apart from the covertape;

a chamber moving frame, which, while fixing the chamber for storing reaction solution, includes a movement pathway for the chamber for storing reaction solution to move toward the covertape breaking unit;

a mixing unit, which, while receiving the reaction solution released as the covertape is removed, allows the reaction solution to contact with a sample injection unit of the insertion-type sample cartridge to be mixed with a biological sample being released thereby forming a mixed solution;

a sample introduction unit, in which a sample is fixed to be able to react with the mixed solution in the mixing unit;

a measurement unit for optical measurement of the reaction result; and a flow path which connects the mixing unit, sample introduction unit, and measurement unit;

in which, the insertion-type sample cartridge includes:

a sample injection unit of a capillary shape, which collects and stores a liquid biological sample and in which a sample injection unit capable of supplying the stored biological sample to the reaction cartridge is provided; and a protrusion, which comes into contact with the chamber for storing reaction solution of the reaction cartridge and thereby transports the chamber for storing reaction solution to the covertape breaking unit when the insertion-type sample cartridge is inserted into the receiving unit of the reaction cartridge.

In particular, as the insertion-type sample cartridge is inserted into the reaction cartridge, simultaneously, the chamber for storing a reaction solution moves toward the covertape breaking unit and may thereby break the covertape; the reaction cartridge may include a plurality of sample introduction units; the mixed solution of the released reaction solution and the biological sample may be transported to the measurement unit or sample introduction unit along the flow path by the gravity and centrifugal force caused by the rotation of the entire cartridge; the reaction cartridge may further include a waste liquid treatment unit for treating a mixed solution of the biological sample, reaction solution, and chemical sample after the measurement; and the reaction cartridge may further include an air outlet for smooth movement and collection of the waste liquid.

Meanwhile, the enzymatic method for quantitative analysis of HbA1c according to the present invention consists of the following four chemical reactions.

The first reaction is a hemolytic reaction of a blood sample, in which red blood cells of the blood are destroyed and thereby hemoglobin is freed. In particular, the reaction solution used for the purpose of hemolysis may be prepared by various methods (e.g., pH adjustment, use of a surfactant, etc.). For example, as the surfactant, zwitterionic surfactants such as 3-(dimethyl(3-tetradecanamidopropyl)ammonio) propane-1-sulfonate; 4-(dimethyl(3-tetradecanamidopropyl) ammonio)butane-1-sulfonate; 3-(dimethyl(tetradecyl)ammonio)propane-1-sulfonate, etc. may be used.

The second reaction is a reaction to cleave HbA1c molecules using a proteolytic enzyme, and various enzymes (e.g., protease A, protease N, dispase, pronase, neutral protease, Glu-C, papain, trypsin, pepsin, etc.) may be used. For example, proteolytic enzymes can selectively cleave only the glucose-Val-His of the N-terminal β-chain of HbA1c, which is released by hemolysis of red blood cells, to obtain a monomolecular fructosyl amino acid.

The third reaction is a reaction in which glycated peptide or glycated amino acid molecules, which are produced via cleavage by a proteolytic enzyme, are oxidized by an oxidizing enzyme called fructosyl peptide oxidase (FPOX), and hydrogen peroxide can be produced by the third reaction.

The fourth reaction is a chemical reaction for color development, in which the hydrogen peroxide ($H_2O_2$) is oxidized using peroxidase (POD), and the electrons released by the oxidation reduces the color developing reagent and the substrate resulting in discoloration.

The HbA1c concentration in the blood sample can be quantified by comparing the amount of total hemoglobin measured through the discoloration with the amount of total hemoglobin immediately after hemolysis from the red blood cells before protease treatment.

Specifically, the amount of HbA1c relative to the amount of total hemoglobin can be expressed as a percentage. Additionally, the amount of total hemoglobin can be measured using a spectroscopic device such as UV/vis.

For the quantitative analysis of HbA1c through the enzymatic method, it will be explained that, for example, the four reactions are performed in a biochemical analysis cartridge according to the present invention and that the quantitative analysis of HbA1c is performed through the cartridge structures illustrated in FIGS. 2 to 6. However, the kit for quantitative analysis of HbA1c according to the present invention is not limited thereto.

To perform the analysis, the blood is collected and stored through a sample injection unit 101 of an injection-type sample cartridge 100. Then, the insertion-type sample cartridge 100 was inserted into a receiving unit 201 of a reaction cartridge 200, and a chamber for storing reaction solution 301 was transported through a chamber moving frame 203 by a protrusion 102 of an insertion-type sample cartridge, and as the covertape 302 attached to the chamber for storing reaction solution comes into contact with a covertape breaking unit 202, the reaction solution within the storage chamber was released and moved to a mixing unit 204. The released reaction solution comes into contact with the sample injection unit 101 of the sample and is mixed with the blood sample, and as a result, hemolysis of the blood sample and the reaction solution occurs. After the completion of hemolysis, the reagent fixed by the blood sample is dissolved in a first sample introduction unit, where one of the proteolytic enzyme, FPOX, and POD is fixed, and an enzymatic reaction is induced by the same.

Hemolysis is performed in the mixing unit 204, and the reaction solution, in which an enzymatic reaction by the first sample introduction unit is completed is transported to a measurement unit 207 through a flow path 206 by rotation and gravity. For the reaction solution transported to the measurement unit 207, the concentration of hemolyzed total hemoglobin can be measured using a UV-Vis spectrophotometer based on the absorbance that appears at 535 nm.

The reaction solution, in which the measurement of total hemoglobin is completed, is transported to a second sample introduction unit by the rotation of a cartridge. In the second sample introduction unit, a reagent, in which two remaining enzymes excluding the enzyme fixed in the first sample introduction unit are mixed, and a color developing reagent are fixed, and the two enzyme reagents and the color developing reagent were constituted in a face-to-face structure.

The reaction solution transported to the second sample introduction unit undergoes both the enzyme reaction and the color development reaction. The reaction solution where both the enzyme reaction and the color development reaction are completed is again transported to the measurement unit 207 by the rotation of the cartridge. Then, the concentration of glycated hemoglobin (HbA1c) color-developed by a color development reaction can be measured using a UV-Vis spectrophotometer based on the absorbance that appears at a region near 660 nm.

The waste liquid for which the analysis is completed is transported to a waste liquid treatment unit 208 by the rotation of a cartridge, and the waste liquid is collected by absorbing through the absorbing raw materials within the waste liquid treatment unit 208.

As described above, for the quantitative analysis of HbA1c, two spectroscopic measurements must be performed and this is because HbA1c represents the ratio of glycated hemoglobin to the concentration of total hemoglobin. That is, there is a cumbersome burden for a measurer to carry out an analysis process consisting of many steps, such as a process of pretreatment of a blood sample and a process of attaching a labeling material. However, when HbA1c is analyzed using the kit for quantitative analysis of HbA1c according to the present invention, the measurement of the absolute concentrations of total hemoglobin and HbA1c as well as the performance of the enzyme reaction can be performed in a single cartridge, by transporting the reaction solution through the rotation of the cartridge. In particular, as the insertion-type sample cartridge 100 is inserted into the reaction cartridge 200, simultaneously, the reaction solution (a hemolytic reagent in case of HbA1c analysis) can be automatically released into a mixing unit within the reaction cartridge. As a result, direct intervention of the analysis performer carrying out the analysis in the self-analysis process can be minimized, and can also prevent delays in the analysis time and poor accuracy of the analysis. Additionally, since the chamber for storing reaction solution 301 is provided within the reaction cartridge 200, there is an effect that the release of the reaction solution to the outside before the insertion of the sample cartridge 100 can be prevented.

Although a kit for quantitative analysis of HbA1c according to the present invention has been described above via specific embodiments, the kit may be modified into various forms, and those skilled in the art can make various changes without departing from the scope of the present invention. It will be understood that variations and modifications can be effected.

MODE FOR CARRYING OUT THE INVENTION

Hereinafter, the present invention will be described in detail by Experimental Examples.

However, the following Experimental Examples are only illustrative of the present invention and the present invention is not limited thereto.

Experimental Example 1

Evaluation of Thermal Stability of FPOX Reagents with Time

1. Experimental Method

To evaluate thermal stability of FPOX reagents with time, the FPOX reagents were placed at room temperature (15° C. to 20° C.), 40° C., or 50° C. and the changes occurred were measured.

40 U/mL FPOX dissolved in 50 mM MES (pH 5.5) was dispensed in each well of a separation-type 96 well plate in an amount of 5 μL per well, dried in a 50° C. oven, and packed individually. Each individually packed sample was stored at room temperature (15° C. to 20° C.), 40° C., or 50° C. for a long period of time.

Compositions of the reagents used are as follows.

1. Hemolytic Solution: 100 mM MES-NaOH, pH 6.0, 10 mM $CaCl_2$, 0.5 mM $NaNO_2$, 1.25 mg/mL ASB-14

2. Protease solution: 1.6 mg/mL Pronase (from Roche) 100 mM MES-NaOH, 10 mM $CaCl_2$, 0.5 mM $NaNO_2$, pH 6.0

3. POD Solution: 50 U POD (from TOYOBO) 100 mM MES-NaOH, 10 mM $CaCl_2$, 0.5 mM $NaNO_2$, 1.25 mg/mL ASB-14, pH 6.0

4. DA-67 Solution: 4.8 mg/dL DA 100 mM MES-NaOH, 10 mM $CaCl_2$, 1.25 mg/mL ASB-14, pH 6.0

5. Sample for Measurement: Lyphochek Diabetes Linearity Controls Levels 1 & 4 (from Bio-Rad)

Activity measurement was performed as follows.

1. Protease, a POD solution, and a hemolytic solution are incubated in a 40° C. constant temperature water bath for at least 30 minutes. DA-67 solution is handled with care so as not to be exposed to light.

2. The hemolytic solution (395 μL) and a sample to be measured (Level #1 or #4: 5 μL) are mixed in a tube.

3. The hemolytic solution and the POD solution in an amount of 400 μL each are added to the tube no. 2 and mixed thoroughly.

4. The solution in the tube no. 2 in an amount of 120 μL is added to each well, in which the FPOX reagent to be measured is dispensed/dried, and incubated at 37° C. for 1 minute.

5. The protease solution and the DA-67 solution are each added into a tube in an amount of 100 μL and mixed at a 1:1 ratio.

6. The solution in the tube no. 5 in an amount of 80 μL is added to the $4^{th}$ well and incubated at 37° C. After 1, 2, and 3 minutes of the incubation, the absorbance is measured at wavelengths of 663 nm and 750 nm, respectively.

7. A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.

2. Experimental Results

As a result of examining the residual activity with time, it was confirmed that 95% or more of the initial activity was maintained even after 312 hours when stored at room temperature, whereas the residual activity was reduced to 65% of the initial activity when stored at 40°, and the activity was completely lost after 312 hours when stored at 50° C.

From the above results, it was confirmed that in a case of a sample which was dispensed/dried with FPOX alone, the decrease in activity with time was significant proportional to the temperature being applied, as shown in FIG. 7. From the result, it was confirmed that there is a need to improve thermal stability of the FPOX reagent when the FPOX reagent is used after drying.

Experimental Example 2

Evaluation 1 of Thermal Stability of FPOX Reagents by Stabilizer Type

1. Experimental Method

A reagent mixture, in which FPOX (40 U/mL) dissolved in 50 mM MES (pH 5.5) and POD 400 U/mL (400 U/mL) are mixed, dispensed in an amount of 10 μL, was treated with each of 100 mM trehalose, 50 mM mannitol, or 1 wt % dextran, which serves as a protein stabilizer in the present invention, and the stability was evaluated at 50° C.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14

2. Protease solution: 1.6 mg/mL Pronase (from Roche) 100 mM MES-NaOH, 10 mM $CaCl_2$, 0.5 mM $NaNO_2$, pH 6.0

3. DA-67 solution: 4.8 mg/dL DA 100 mM MES-NaOH, 10 mM $CaCl_2$, 1.25 mg/mL ASB-14, pH 6.0

Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.

2. The hemolytic solution (395 μL) and a sample to be measured (Level #1 or #4: 5 μL) are mixed in a tube.

3. The hemolytic solution in an amount of 800 μL is added to the tube no. 2 and mixed thoroughly.

4. The solution in the tube no. 2 in an amount of 120 μL is added to each well, in which the (FPOX+POD) reagent to be measured is dispensed/dried, and incubated at 37° C. for 1 minute.

5. The protease solution and the DA-67 solution are each added into a tube in an amount of 100 μL and mixed at a 1:1 ratio.

6. The solution in the tube no. 5 in an amount of 80 μL is added to the $4^{th}$ well and incubated at 37° C. After 1, 2, and 3 minutes of the incubation, the absorbance is measured at wavelengths of 663 nm and 750 nm, respectively.

7. A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.

2. Experimental Results

In a case of a reagent mixture of an enzyme alone, the activity was rapidly decreased as time passed over 120 hours, and the activity was completely lost after 500 hours. In a case where 50 mM mannitol was included, a similar change was shown, but a little activity (about 10%) was shown to remain even after 500 hours. Meanwhile, in a case of a sample where 100 mM trehalose or 1 wt % dextran is included, an activity of almost 95% or higher was maintained up to the time point of 200 hours, but the activity began to decrease thereafter and decreased to 75% after 500 hours.

That is, as shown in FIG. 8, in cases of trehalose and dextran, they significantly increased the thermal stability of the (FPOX+POD) mixture. In a case of POD, it is conventionally known that the thermal stability of the reagent itself is excellent, and thus it was confirmed from the experimental results of the present invention that trehalose and dextran can significantly improve the thermal stability of FPOX.

Experimental Example 3

Evaluation 2 of Thermal Stability of FPOX Reagents by Stabilizer Type

1. Experimental Method

A reagent mixture, in which FPOX (40 U/mL) and POD 400 U/mL (400 U/mL) are mixed, dispensed in an amount of 5 μL, and reagents to which each of 500 mM trehalose, 500 mM mannitol, 5 wt % dextran, 5 wt % diethylaminoethyl cellulose-Dextran (DEAE-dextran), 5 wt % polyethylene glycol (PEG), 5 wt % polyvinylpyrrolidone (PVP), 5 wt % polyvinyl alcohol (PVA), 5 wt % polyacryl acid (PAA), 5 wt % para-aminosalicylic acid (PAS), or 5 wt % corn dextrin (CD) was added, was dried at 50° C. for 120 minutes and packaged and stored at 50° C., and the thermal stability with time was evaluated via HbA1c measurement.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14

2. Protease solution: 1.6 mg/mL Pronase (from Roche) 100 mM MES-NaOH, 10 mM $CaCl_2$, 0.5 mM $NaNO_2$, pH 6.0

3. DA-67 solution: 4.8 mg/dL DA 100 mM MES-NaOH, 10 mM $CaCl_2$, 1.25 mg/mL ASB-14, pH 6.0

4. Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.

2. The hemolytic solution (395 μL) and a sample to be measured (Level #1 or #4: 5 μL) are mixed in a tube.

3. The hemolytic solution in an amount of 800 μL is added to the tube no. 2 and mixed thoroughly.

4. The solution in the tube no. 2 in an amount of 120 μL is added to each well, in which the (FPOX+POD) reagent to be measured is dispensed/dried, and incubated at 37° C. for 1 minute.

5. The protease solution and the DA-67 solution are each added into a tube in an amount of 100 μL and mixed at a 1:1 ratio.

6. The solution in the tube no. 5 in an amount of 80 μL is added to the $4^{th}$ well and incubated at 37° C. After 1, 2, and 3 minutes of the incubation, the absorbance is measured at wavelengths of 663 nm and 750 nm, respectively.

A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.

2. Experimental Results

As a result of examination of the residual activity with time, while the activity in the (FPOX+POD) alone composition, where no stabilizer is added, was almost disappeared, in the sample in which trehalose, dextran, DEAE-dextran, and polyacrylic acid (PAA) are included at high concentration, the activity was at a level of 90% or higher thus confirming that these materials contribute to the maintenance of stability. Although polyvinyl alcohol (PVP), dextrin (CD), mannitol, etc. also had a stabilizing effect, but the effects were lower than those of trehalose, dextran, DEAE-dextran, polyacrylic acid (PAA). Polyethylene glycol (PEG) and para-aminosalicylic acid (PAS). Based on the above results, there was a need to examine whether combinations of trehalose, which has a high stabilizing effect, and polymers (e.g., dextran, DEAE-dextran, and polyacrylic acid (PAA)) may exhibit an improved effect.

Experimental Example 4

Evaluation of Thermal Stability of FPOX Reagents According to Buffer Type

1. Experimental Method

FPOX (40 U/mL) was treated with 10 mM MES-NaOH buffer (pH 5.5), 10 mM MES-NaOH buffer (pH 6.0), 100 mM phosphate buffer (pH 6.5: manufacturer: TOYOBO), or 100 mM phosphate buffer (pH 7.0), and then dispensed to each well of a separation-type 96 well plate in an amount of 5 µL, dried in a 50° C. oven for 2 hours, and packaged individually. Each individually packaged sample was stored at 40° C. and 50° C. for a long period of time. The thermal stability of each individually package sample was evaluated via HbA1c measurement at temperature conditions of 40° C. and 50° C.

Compositions of the reagents used are as follows.

1. Hemolytic Solution: 100 mM MES-NaOH, pH 6.0, 10 mM $CaCl_2$, 0.5 mM $NaNO_2$, 1.25 mg/mL ASB-14
2. Protease solution: 1.6 mg/mL Pronase (from Roche) 100 mM MES-NaOH, 10 mM $CaCl_2$, 0.5 mM $NaNO_2$, pH 6.0
3. POD Solution: 50 U PD (from TOYOBO) 100 mM MES-NaOH, 10 mM $CaCl_2$, 0.5 mM $NaNO_2$, 1.25 mg/mL ASB-14, pH 6.0
4. DA-67 Solution: 4.8 mg/dL DA 100 mM MES-NaOH, 10 mM $CaCl_2$, 1.25 mg/mL ASB-14, pH 6.0
5. Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.
2. The hemolytic solution (395 µL) and a sample to be measured (Level #1 or #4: 5 µL) are mixed in a tube.
3. The hemolytic solution and the POD solution each in an amount of 400 µL are added to the tube no. 2 and mixed thoroughly.
4. The solution in the tube no. 2 in an amount of 120 µL is added to the well, in which the (FPOX+POD) reagent to be measured is dispensed/dried, and incubated at 37° C. for 1 minute.
5. The protease solution and the DA-67 solution are each added into a tube in an amount of 100 µL and mixed at a 1:1 ratio.
6. The solution of tube no. 5 in an amount of 80 µL is added to the 4$^{th}$ well and incubated at 37° C. After 1, 2, and 3 minutes of the incubation, the absorbance is measured at wavelengths of 663 nm and 750 nm, respectively.

A linear equation is made such that the absorbance of 2 minutes after incubation at wavelengths of 663 nm and 750 nm is calculated to be used as a Y axis, and the theoretical molar concentration (µM) of HbA1c is calculated from the HbA1c % concentration of the sample to be measured to be used as an X axis, and the Slope and Y inter. are calculated.

2. Experimental Results

As shown in FIG. 10 and FIG. 11, when phosphate buffer is used among buffers of various kinds and pHs, it was confirmed that the thermal stability of FPOX itself was significantly improved compared to other compositions. From these results, it was confirmed that not only the effect due to the addition of a stabilizer (e.g., trehalose), but also additional improvement in stability can be expected by changing the buffer composition.

Experimental Example 5

Evaluation of Thermal Stability of FPOX According to Concentration of Trehalose Treatment 1. Experimental Method The (FPOX+POD) mixture was prepared according to the composition (40 U/mL FPOX, 400 U/mL POD, 100 mM PB pH 6.5, 1.5 mg/mL 3-(N,N-dimethylmyristylammonio)propanesulfonate, +0 mM, 100 mM, 200 mM, 300 mM, 400 mM, and 500 mM trehalose), dispensed each in an amount of 5 µL, and dried in a 50° C. oven for 2 hours. Then, the residual activity of the resultant with time was examined while storing in a 50° C. oven.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14
2. Protease solution: 1.6 mg/mL Pronase (from Roche) 100 mM MES-NaOH, 10 mM $CaCl_2$, 0.5 mM $NaNO_2$, pH 6.0
3. DA-67 solution: 4.8 mg/dl DA 100 mM MES-NaOH, 10 mM $CaCl_2$, 1.25 mg/mL ASB-14, pH 6.0
4. Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.
2. The hemolytic solution (395 µL) and a sample to be measured (Level #1 or #4: 5 µL) are mixed in a tube.
3. The hemolytic solution in an amount of 800 µL is added to the tube no. 2 and mixed thoroughly.
4. The solution in the tube no. 2 in an amount of 120 µL is added to the well, in which the (FPOX+POD) reagent to be measured is dispensed/dried, and incubated at 37° C. for 1 minute.
5. The protease solution and the DA-67 solution are each added into a tube in an amount of 100 µL each and mixed at a 1:1 ratio.
6. The solution of the tube no. 5 in an amount of 80 µL is added to the 4$^{th}$ well and incubated at 37° C. After 1, 2, and 3 minutes of the incubation, the absorbance is measured at wavelengths of 663 nm and 750 nm, respectively.
7. A linear equation is made such that the absorbance of 2 minutes after incubation at wavelengths of 663 nm and 750 nm is calculated to be used as a Y axis, and the theoretical molar concentration (µM) of HbA1c is calculated from the HbA1c % concentration of the sample to be measured to be used as an X axis, and the Slope and Y inter. are calculated.

2. Experimental Results

As shown in FIG. 12, trehalose was shown to improve the thermal stability of FPOX in a concentration-dependent manner.

In cases of a sample where trehalose is not included and a sample where trehalose is included at a concentration of 100 mM to 200 mM, the activity began to decrease rapidly and almost all activity was disappeared after 360 hours. Meanwhile, the composition in which trehalose is included at a concentration of 300 mM to 500 mM was more stable to thermal stress, but the activity was rapidly decreased after 200 hours. The composition in which 500 mM trehalose is included, considering the results that it is very stable to heat for a long period of time thus far, it is possible that there was a difficulty in the effect of 3-(N,N-dimethylmyristylammonio) propanesulfonate, which is the surfactant to increase dissolution rate during re-dissolution after drying the present experiment, or the combination of phosphate buffer, surfactant, and FPOX.

Experimental Example 6

Evaluation of Thermal Stability of FPOX According to Combination Treatment of Stabilizers 1. Experimental Method After treating FPOX (40 U/mL, 5 µL) with trehalose at a concentration of 500 mM alone, or treating with 500 mM trehalose in combination with dextran, DEAD or PAA at a concentration of 1 wt % to 5 wt %, and then dissolving the resultant in 100 mM phosphate buffer (pH 6.5), drying at 80° C. for 10 minutes and packaged, and the thermal stability with time was evaluated via HbA1c measurement while storing at 50° C.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14

2. Protease solution: 4,000 U/mL Neutral Protease (from TOYOBO) 100 mM MES-NaOH, 10 mM $CaCl_2$, 0.5 mM $NaNO_2$, pH 6.0

3. POD Solution: 50 U/mL PD (from TOYOBO) 100 mM MES-NaOH, 10 mM $CaCl_2$, 0.5 mM $NaNO_2$, 1.25 mg/mL ASB-14, pH 6.0

4. DA-67 Solution: 4.8 mg/dL DA 100 mM MES-NaOH, 10 mM $CaCl_2$, 1.25 mg/mL ASB-14, pH 6.0

5. Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.

2. The hemolytic solution (395 µL) and a sample to be measured (Level #1 or #4: 5 µL) are mixed in a tube.

3. The hemolytic solution and the POD solution in an amount of 400 µL each are added to the tube no. 2 and mixed thoroughly.

4. The solution in the tube no. 2 in an amount of 120 µL is added to the well, in which the (FPOX+POD) reagent to be measured is dispensed/dried, and incubated at 37° C. for 1 minute.

5. The protease solution and the DA-67 solution are each added into a tube in an amount of 100 µL and mixed at a 1:1 ratio.

6. The solution of the tube no. 5 in an amount of 80 µL is added to the $4^{th}$ well and incubated at 37° C. After 1, 2, and 3 minutes of the incubation, the absorbance is measured at wavelengths of 663 nm and 750 nm, respectively.

7. A linear equation is made such that the absorbance of 2 minutes after incubation at wavelengths of 663 nm and 750 nm is calculated to be used as a Y axis, and the theoretical molar concentration (µM) of HbA1c is calculated from the HbA1c % concentration of the sample to be measured to be used as an X axis, and the Slope and Y inter. are calculated.

2. Experimental Results

As shown in FIG. 13, it was confirmed that FPOX was treated with trehalose alone the thermal stability of FPOX was significantly improved compared to when FPOX was treated with trehalose in combination with other types of stabilizers.

In the conditions of drying at 80° C. for 10 minutes, the initial activity was maintained at a level of about 95% to 100% in all of the composition, where 1% dextran and 5% PAA were excluded. However, it was confirmed that even when 500 mM trehalose was treated alone, it was possible that the FPOX activity could be maintained at 50° C. for more than one month.

Experimental Example 7

Evaluation of Thermal Stability of FPOX According to Treatment with Trehalose and Buffer 1. Experimental Method FPOX containing trehalose at a concentration of 500 mM was dispensed in a 100 mM phosphate buffer (pH 6.5), dried at 80° C. for 10 minutes and packaged, and the thermal stability with time was evaluated via HbA1c measurement while storing at 50° C.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14

2. Protease solution: 4,000 U/mL Neutral Protease (from TOYOBO) 100 mM MES-NaOH, 10 mM $CaCl_2$, 0.5 mM $NaNO_2$, pH 6.0

3. POD Solution: 50 U/mL PD (from TOYOBO) 100 mM MES-NaOH, 10 mM $CaCl_2$, 0.5 mM $NaNO_2$, 1.25 mg/mL ASB-14, pH 6.0

4. DA-67 Solution: 4.8 mg/dL DA 100 mM MES-NaOH, 10 mM $CaCl_2$, 1.25 mg/mL ASB-14, pH 6.0

5. Sample for Measurement: Lyphochek Diabetes Linearity Controls Levels 1 & 4 (from Bio-Rad)

Activity measurement was performed as follows.

1. Protease and a hemolytic solution are incubated in a 40° C. constant temperature water bath for at least 30 minutes. DA-67 solution is handled with care so as not to be exposed to light.

2. The hemolytic solution (395 µL) and a sample to be measured (Level #1 or #4: 5 µL) are mixed in a tube.

3. The hemolytic solution and the POD solution in an amount of 400 µL each are added to the tube no. 2 and mixed thoroughly.

4. The solution in the tube no. 2 in an amount of 120 µL is added to the well, in which the (FPOX+POD) reagent to be measured is dispensed/dried, and incubated at 37° C. for 1 minute.

5. The protease solution and the DA-67 solution are each added into a tube in an amount of 100 µL and mixed at a 1:1 ratio.

6. The solution of the tube no. 5 in an amount of 80 µL is added to the $4^{th}$ well and incubated at 37° C. After 1, 2, and 3 minutes of the incubation, the absorbance is measured at wavelengths of 663 nm and 750 nm, respectively.

7. A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.

2. Experimental Results

As shown in FIG. 14, it was confirmed that the FPOX treated with phosphate buffer (pH 6.5) and trehalose maintained stability at 50° C. for about 70 days or more.

This corresponds to 930 days (2.5 years) when the conversion method of a general enzyme stability test (where 1 day at 50° C. is calculated as 12.9 days at room temperature).

In FIG. 14, Slope represent activity and Inter (Y intercept) represents the background absorbance of the measurement system itself (the absorbance value in the absence of a sample).

Experimental Example 8

Evaluation of Homogeneity of FPOX According to Addition of Neo Protein Savor (NPS)

To evaluate the solubility of each of a reagent mixture (10 mL), in which FPOX (200 U/mL) dissolved in 100 mM PB (pH 6.5) and 500 mM trehalose are mixed, and a composition (10 mL solution), to which Neo Protein Saver (NPS, TOYOBO), which is a commercially available protein stabilizer containing amino acids and peptides as active ingredients, is additionally mixed to a concentration of 17 mg/mL, the turbidity was measured at 330 nm using the UV-Vis spectrophotometer. The solutions were measured every hour until the lapse of 3 hours from immediately after the preparation of the solutions, and the proportion of the composition containing NPS was calculated based on the OD value of the composition containing only 500 mM trehalose set as 100%.

As shown in FIG. 15, as a result of comparing the solution where NPS was contained to FPOX to a concentration of 17 mg/mL (Experimental Group) and the solution where NPS not included (Control Group), it was observed that the solution of Experimental Group showed lower turbidity and compared to that of Control Group (about 20%) and was transparent. This could be visually detected indicating that NPS affected the solubility of FPOX.

Based on the above results, the reagent composition in which FPOX (40 U/mL) dissolved in 100 mM PB (pH 6.5) and 500 mM trehalose are mixed, and a composition to which NPS is additionally mixed to a concentration of 17 mg/mL, were each dispensed in an amount of 5 μL, dried at 80° C. for 10 minutes, and then packed, stored at 50° C., and the thermal stability after 1, 6, and 14 days was evaluated via HbA1c measurement.

Compositions of other reagents used are as follows.

1. Hemolytic Solution: 100 mM MES-NaOH, pH 6.0, 10 mM $CaCl_2$, 0.5 mM $NaNO_2$, 1.25 mg/mL ASB-14
2. Protease solution: 4,000 U/mL Neutral Protease (from TOYOBO) 100 mM MES-NaOH, 10 mM $CaCl_2$, 0.5 mM $NaNO_2$, pH 6.0
3. POD Solution: 50 U/mL PD (from TOYOBO) 100 mM MES-NaOH, 10 mM $CaCl_2$, 0.5 mM $NaNO_2$, 1.25 mg/mL ASB-14, pH 6.0
4. DA-67 Solution: 4.8 mg/dL DA 100 mM MES-NaOH, 10 mM $CaCl_2$, 1.25 mg/mL ASB-14, pH 6.0
5. Sample for Measurement: Lyphochek Diabetes Linearity Controls Levels 1 & 4 (from Bio-Rad)

Activity measurement was performed as follows.

1. Protease, a POD solution, and a hemolytic solution are incubated in a 40° C. constant temperature water bath for at least 30 minutes. DA-67 solution is handled with care so as not to be exposed to light.
2. The hemolytic solution (395 μL) and a sample to be measured (Level #1 or #4: 5 μL) are mixed in a tube.
3. The hemolytic solution and the POD solution in an amount of 400 μL each are added to the tube no. 2 and mixed thoroughly.
4. The solution in the tube no. 2 in an amount of 120 μL is added to the well, in which the (FPOX+POD) reagent to be measured is dispensed/dried, and incubated at 37° C. for 1 minute.
5. The protease solution and the DA-67 solution are each added into a tube in an amount of 100 μL and mixed at a 1:1 ratio.
6. The solution of the tube no. 5 in an amount of 80 μL is added to the $4^{th}$ well and incubated at 37° C. After 1, 2, and 3 minutes of the incubation, the absorbance is measured at wavelengths of 663 nm and 750 nm, respectively.
7. A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.
8. The ratios of the Slope calculated in Experimental Group and Control Group are calculated, respectively.

2. Experimental Results

As shown in FIG. 16, it was confirmed that the FPOX mixture in which trehalose and NPS are included maintained a similar level of thermal stability for 14 days, compared to a case where FPOX was treated with trehalose. As a result, it was confirmed that the homogeneity of the solution could be improved while securing thermal stability, by further adding NPS to the FPOX mixture solution. It is contemplated that the homogeneity of the solution will be able to contribute to the overall quality in the course of preparation of the corresponding solution into a cartridge form.

Experimental Example 9

Evaluation of Thermal Stability of Compositions Containing FPOX, Trehalose, NPS, and Buffer According to Time 1. Experimental Method A composition containing FPOX (180 U/mL), 500 mM trehalose, NPS (17.5 mg/mL), and 100 mM phosphate buffer (pH 6.5) was prepared, and then dispensed into the FPOX position of a reagent cartridge (FIG. 1) in an amount of 5 μL, dried at 80° C. for 10 minutes, packaged and stored, and the thermal stability with time was evaluated via HbA1c measurement.

Compositions of other reagents used are as follows.

1. Hemolytic Solution: 100 mM MES-NaOH, pH 6.0, 10 mM $CaCl_2$, 1.25 mg/mL ASB-14
2. Protease and POD solution: 40,000 U/mL Neutral Protease (from TOYOBO), 800 U/mL PD (from TOYOBO), 100 mM MES-NaOH, 100 mM Trehalose, pH 6.0
3. Oxidizing solution: 300 mM $NaNO_2$, 0.005 wt % D10, pH 8.0

4. DA-67 Solution: 40 mg/dL DA, DW

5. Sample for Measurement: Lyphochek Diabetes Linearity Controls Level 4 (from Bio-Rad)

Activity measurement was performed as follows.

1. An FPOX cartridge, which has been dispensed at 50° C. for a certain period of time, is recovered, and other solutions are dispensed and assembled/fused and attached to produce a reagent cartridge.

2. The measurement starts by clicking the "RUN" button in the A1Care Analyzer's measurement window.

3. After injecting the Control sample to be measured into the capillary tube of the sample collector, the sample collector is mounted on the cartridge, and the prepared cartridge is mounted after opening the door of the A1Care Analyzer.

4. The sample collector is inserted into the inside of the instrument to the end, destroys the solution cell mounted inside of the cartridge, and thereby mix a hemolytic solution and a sample in the sample collector.

5. The door of the A1Care Analyzer is closed and the reaction starts.

6. After completion of the measurement in about 4 minutes, the value of HbA1c % is confirmed.

2. Experimental Results

As shown in FIG. 17, it was confirmed that the composition containing FPOX, trehalose, NPS, and buffer maintained stability at a temperature of 50° C. for about 63 days or more, even when prepared by dispensing/drying on a cartridge.

Experimental Example 10

Evaluation of Stability of Pronase According to Stabilizer Type

1. Experimental Method

A composition containing pronase (0.1 mg/mL), 100 mM MES-NaOH buffer, 10 mM $CaCl_2$, and 0.5 mM $NaNO_2$ (pH 6.0) was prepared, and a stabilizer was further added thereto at a concentration of 100 mM or 1 wt %, and the thermal stability was evaluated.

In particular, the stabilizer used in the present experiment was classified into low molecular weight stabilizers and high molecular weight stabilizers. As the low molecular weight stabilizer, trehalose, trimethylamine N-oxide (TMA-NO), Spermine (SP), Spermidine (SPD), arginine (Arg), Sarcosine (Src), betaine, and mannitol were used, and as the high molecular weight stabilizer, dextran, PEG, PVP, and dextrin were used.

2. Experimental Results

Referring to FIG. 18 where a low molecular weight stabilizer was treated, trehalose was shown to maintain stability of pronase up to about 300 hours, and additionally, induced a stabilizing effect of 80% or higher, with respect to arginine, Sarcosine, mannitol, Spermine, etc.

Referring to FIG. 19 where a high molecular weight stabilizer was treated, dextran was shown to maintain stability of pronase up to about 300 hours, and dextrin was shown to maintain activity up to about 75%, however, PEG and PVP were shown not to be able to induce thermal stability of pronase.

Experimental Example 11

Evaluation of Stability of Pronase by Treatment of Combined Stabilizers

1. Experimental Method

To evaluate the thermal stability of the protease reagent with time, the protease reagent was placed at 50° C. and the changes were measured. A composition was prepared, in which a high molecular weight compound (1 M or 10%) was mixed with pronase (0.1 mg/mL) dissolved in 100 mM MES (pH 6.0), and dispensed into each well of a separation-type 96 well plate in an amount of 5 μL, dried in a 50° C. oven for 2 hours, and packaged individually. Each individually packaged sample was stored at 50° C. for a long period of time.

Compositions of other reagents used are as follows.

1. Hemolytic Solution: 100 mM MES-NaOH, pH 6.0, 10 mM $CaCl_2$, 2 mM $NaNO_2$, 0.75 mg/mL ASB-14

2. FPOX Solution: 5 U/mL FPOX (from TOYOBO), 100 mM MES-NaOH, pH 6.0, 10 mM $CaCl_2$, 2 mM $NaNO_2$, 0.75 mg/mL ASB-14

3. POD Solution: 50 U POD (from TOYOBO), 100 mM MES-NaOH, pH 6.0, 10 mM $CaCl_2$, 2 mM $NaNO_2$, 0.75 mg/mL ASB-14

4. DA-67 Solution: 4.8 mg/dL DA 100 mM MES-NaOH pH 6.0, 10 mM $CaCl_2$, 0.75 mg/mL ASB-14

5. Sample for Measurement: Lyphochek Diabetes Linearity Controls Levels 1 & 4 (from Bio-Rad)

Activity measurement was performed as follows.

1. Protease, a POD solution, and a hemolytic solution are incubated in a 40° C. constant temperature water bath for at least 30 minutes. DA-67 solution is handled with care so as not to be exposed to light.

2. The hemolytic solution (395 μL) and a sample to be measured (Level #1 or #4: 5 μL) are mixed in a tube.

3. The FPOX solution and the POD solution in an amount of 400 μL each are added to the tube no. 2 and mixed thoroughly.

4. The solution in the tube no. 2 in an amount of 120 μL is added to the well, in which the protease reagent to be measured is dispensed/dried, and incubated at 37° C. for 1 minute.

5. The protease solution and the DA-67 solution are each added into a tube in an amount of 100 μL and mixed at a 1:1 ratio.

6. The solution of the tube no. 5 in an amount of 80 μL is added to the $4^{th}$ well and incubated at 37° C. After 1, 2, and 3 minutes of the incubation, the absorbance is measured at wavelengths of 663 nm and 750 nm, respectively.

7. A linear equation is made such that the absorbance of 2 minutes after incubation at wavelengths of 663 nm and 750 nm is calculated to be used as a Y axis, and the theoretical molar concentration (μM) of HbA1c is calculated from the HbA1c % concentration of the sample to be measured to be used as an X axis, and the Slope and Y inter. are calculated.

2. Experimental Results

As shown in FIG. 20, it was confirmed that even when the combination of trehalose with other kinds of compounds (dextran, PEG, Man, or Src) did not induce a synergistic effect, and there was no significant difference in stability compared to when trehalose was used alone. However, when trehalose is mixed with other types of high molecular weight compounds, the viscosity of the solution can be increased and was thus thought to be advantageous for dispension and drying.

Experimental Example 12

Evaluation of Thermal Stability of Neutral Protease According to Stabilizer Type 1. Experimental Method To evaluate the thermal stability of the protease reagent with time, the protease reagent was placed at 50° C. and the changes were measured. A composition was prepared, in which a high molecular weight compound (100 mM or 1%) was mixed with neutral protease (TOYOBO) (0.2 mg/mL) dissolved in 100 mM MES (pH 6.0), and dispensed into each well of a separation-type 96 well plate in an amount of 5 µL, dried in a 50° C. oven for 2 hours, and packaged individually. Each individually packaged sample was stored at 50° C. for a long period of time.

Compositions of other reagents used are as follows.

1. Hemolytic Solution: 100 mM MES-NaOH, pH 6.0, 10 mM $CaCl_2$, 2 mM $NaNO_2$, 0.75 mg/mL ASB-14
2. FPOX Solution: 5 U/mL FPOX (from TOYOBO), 100 mM MES-NaOH, pH 6.0, 10 mM $CaCl_2$, 2 mM $NaNO_2$, 0.75 mg/mL ASB-14
3. POD Solution: 50 U POD (from TOYOBO), 100 mM MES-NaOH, pH 6.0, 10 mM $CaCl_2$, 2 mM $NaNO_2$, 0.75 mg/mL ASB-14
4. DA-67 Solution: 4.8 mg/dL DA 100 mM MES-NaOH pH 6.0, 10 mM $CaCl_2$, 0.75 mg/mL ASB-14
5. Sample for Measurement: Lyphochek Diabetes Linearity Controls Levels 1 & 4 (from Bio-Rad)

Activity measurement was performed as follows.

1. Protease, a POD solution, and a hemolytic solution are incubated in a 40° C. constant temperature water bath for at least 30 minutes. DA-67 solution is handled with care so as not to be exposed to light.
2. The hemolytic solution (395 µL) and a sample to be measured (Level #1 or #4: 5 µL) are mixed in a tube.
3. The FPOX solution and the POD solution in an amount of 400 µL each are added to the tube no. 2 and mixed thoroughly.
4. The solution in the tube no. 2 in an amount of 120 µL is added to the well, in which the protease reagent to be measured is dispensed/dried, and incubated at 37° C. for 1 minute.
5. The hemolytic solution and the DA-67 solution are each added into a tube in an amount of 100 and mixed at a 1:1 ratio.
6. The solution of the tube no. 5 in an amount of 80 is added to the $4^{th}$ well and incubated at 37° C. After 1, 2, and 3 minutes of the incubation, the absorbance is measured at wavelengths of 663 nm and 750 nm, respectively.
7. A linear equation is made such that the absorbance of 2 minutes after incubation at wavelengths of 663 nm and 750 nm is calculated to be used as a Y axis, and the theoretical molar concentration (µM) of HbA1c is calculated from the HbA1c % concentration of the sample to be measured to be used as an X axis, and the Slope and Y inter. are calculated.

2. Experimental Results

As shown in FIG. 21, neutral protease basically has higher thermal stability than pronase, and thus there is no difference between a composition containing the enzyme alone and a composition containing trehalose, mannitol, and dextran. Rather, the activity of the composition containing arginine or Spermine was significantly lowered.

As shown in FIG. 22, it was confirmed that when the enzyme is used alone, the value of Y inter. significantly increases with time. In contrast, in a case where trehalose, arginine, Spermine, etc. are mixed, the increase of the background was not observed. From these results, it is contemplated that a composition containing trehalose in which the activity and background values are both stably maintained is suitable as a stabilizer.

Experimental Example 13

Evaluation of Thermal Stability of $NaNO_2$ According to Stabilizer Treatment 1. Experimental Method Since it is not possible to mix $NaNO_2$ with other enzyme reagents, it is necessary that a composition be prepared and dispensed separately. For the evaluation of the composition, 200 mM $NaNO_2$ was simply dissolved in MES buffer and dried, however, the spots were not spread but dried in the shape of a "sphere" and thus all were destroyed during the process of assembly and fusion/attachment and was thus difficult to use. As such, D10(3-(N,N-dimethylmyristylammonio)propanesulfonate) and trehalose, which are surfactants, were mixed to provide physical property, and the performance was evaluated.

2. Experimental Results

As shown in FIG. 23, it was confirmed that the above prepared composition containing $NaNO_2$, D10, trehalose, and MES buffer maintained the initial value even when placed at 50° C. for more than 400 hours. From this result, it was confirmed that $NaNO_2$ can be separated and dried. Additionally, it was confirmed that the physical shape of the spots varied depending on the presence/absence of trehalose, however, there was no difference in terms of preparation process and performance.

Experimental Example 14

Evaluation of Thermal Stability of Color Developing Reagent According to Stabilizer Treatment 1. Experimental Method "DA-67", which is a formazan-based dye (synthesized from the methylene blue structure), refers to a color developing reagent that is primarily used in the measurement of $H_2O_2$ concentration by using in combination with peroxidase (OD), and is produced and commercially available by the WAKO. Since DA-67 has a large variation in absorbance and thus has a good color developing ability and is thus widely used. However, since the stability of the DA-67 itself is low, it is rapidly decomposed when exposed to light, causing a chromatic change in color from colorless to blue thus making it difficult to handle. As such, the present inventors have performed screening of stabilizers that can minimize self-decomposition due to exposure to light for the purpose of efficient use of DA-67.

2. Experimental Results

As shown in FIG. 24, it was confirmed that poly(acrylic acid sodium salt (PAAS), poly(acrylic acid) (PAA), and trehalose inhibit the increase of Y inter. Compared to the group of DA-67 alone. However, PAAS and PAA accompanied an effect of inhibiting the DA-67 signal itself.

Experimental Example 15

Evaluation of Storage Property of a Kit for Quantitative Analysis of HbA1c According to the Present Invention 1. Experimental Method The stability was confirmed by long-term measurement using a kit for quantitative analysis of HbA1c stored in the cold room of a refrigerator (2° C. to 8° C.) and a constant temperature and constant humidity room (20° C. to 25° C.). The confirmation was proceeded EP25-A Evaluation of Stability of in Vitro Diagnostic Reagents; Approved Guideline and "Safety criteria for medical devices" by the Ministry of Health and Welfare.

The criteria are as follows.

1. After a certain period of time has elapsed, take out the cartridges stored in the cold room of a refrigerator (2° C. to 8° C.) and a constant temperature and constant humidity room (20° C. to 25° C.) 10 at a time and store at room temperature (20° C. to 25° C.) for use.
2. Turn on the power of the A1Care analyzer to prepare measurement.
3. Take out samples to be measured (low & high) under frozen storage 10 to 20 minutes before measurement and stir in room temperature conditions.
4. Place the Low Control sample dropwise on a sample collector and mount on the cartridge body.
5. Open the door of the A1Care analyzer, insert the cartridge, press the sample collector, and close the door of the analyzer.
6. Once the measurement is completed, HbA1c % value is calculated on the touch screen and the value is recorded.
7. The same procedure applied to the High Control sample.
8. Repeat steps 4 to 7. (5 repeated measurements per sample)

When the value is maintained within a range of ±5% based on the initial measurement value (HbA1c %), it is determined that the performance of the cartridge is maintained stably during the period, whereas when the value exceeding ±5% is repeated three or more times in succession, it is determined that the stability is not maintained.

2. Experimental Results

As shown in FIG. 25, the kit for quantitative analysis of HbA1c according to the present invention showed stability of more than 2 years when stored in a refrigerator; and as shown in FIG. 26, the kit for quantitative analysis of HbA1c according to the present invention showed stability of more than 1 year when stored at room temperature.

DESCRIPTION OF REFERENCE NUMERALS

100: insertion-type sample cartridge
101: sample injection unit
102: protrusion
103: sample cartridge handle
104: clamp
200: reaction cartridge
201: receiving unit
202: covertape breaking unit
203: chamber moving frame
204: mixing unit
205: sample introduction unit
206: flow path
207: measurement unit
208: waste liquid treatment unit
209: air outlet
210: reaction cartridge handle
211: fixing groove
301: chamber for storing reaction solution
302: covertape

INDUSTRIAL APPLICABILITY

The kit for quantitative analysis of HbA1c according to the present invention has excellent long-term stability of an enzyme reagent and thus can be effectively used as a kit for quantitative analysis of HbA1c in which the disadvantages of the conventional reagents used in enzyme assays (e.g., storage, accuracy, portability, convenience of use, etc.) is easily improved.

The invention claimed is:

1. A kit for quantitative analysis of glycated hemoglobin (HbA1c), comprising:
   a first composition comprising a saccharide and a nitrite compound;
   a second composition comprising at least one selected from the group consisting of a saccharide, an amino acid, a sugar alcohol, and a polyamine; a proteolytic enzyme; and an oxidizing agent;
   a third composition comprising at least one kind selected from the group consisting of a saccharide and an organic polymer; and a fructosyl amino acid oxidase (FAOD); and
   a fourth composition comprising saccharides and a color developing reagent.

2. The kit as set forth in claim 1, wherein the second composition comprises:
   a secondary first composition comprising at least one selected from the group consisting of a saccharide, an amino acid, a sugar alcohol, and a polyamine; and a proteolytic enzyme; and
   a secondary second composition comprising at least one selected from the group consisting of a saccharide, an amino acid, a sugar alcohol, and a polyamine; and an oxidizing agent.

3. The kit as set forth in claim 1, wherein the saccharide is at least one selected from the group consisting of a monosaccharide, a disaccharide, and a polysaccharide.

4. The kit as set forth in claim 3, wherein:
   the monosaccharide is fructose, galactose, glucose, or mannose;
   the disaccharide is sucrose, lactose, maltose, trehalose, turanose, or cellobiose; and
   the polysaccharide is dextran, diethylamino ethyl-dextran, dextrin, cellulose, or β-glucans.

5. The kit as set forth in claim 1, wherein the amino acid is at least one selected from the group consisting of arginine, sarcosine, alanine, cysteine, aspartic acid, glutamic acid, phenylalanine, glycine, histidine, isoleucine, lysine, leucine, methionine, asparagine, pyrrolysine, proline, glutamine, serine, and threonine.

6. The kit as set forth in claim 1, wherein the sugar alcohol is at least one selected from the group consisting of mannitol, xylitol, sorbitol, maltitol, an erythritol.

7. The kit as set forth in claim 1, wherein the polyamine is at least one selected from the group consisting of spermine, putrescine, spermidine, cadaverine, agmatine, and ornithine.

8. The kit as set forth in claim 1, wherein the organic polymer is at least one selected from the group consisting of polydiene-based, polyalkene-based, polyacrylic acid-based, polyacrylate-based, polyacrylamide-based, polymethacrylic acid-based, polymethacrylate-based, polymethacrylamide-based, polyvinyl ether-based, polyvinyl thioether-based, polyvinyl alcohol-based, polyvinyl ketone-based, polyvinyl halide-based, polyvinyl nitrile-based, polyvinyl ester-based, polystyrene-based, polyphenylene-based, polyoxide-based, polycarbonate-based, polyester-based, polyanhydride-based, polyurethane-based, polysulfonate-based, nitroso-polymer-based, polysiloxane-based, polysulfide-based, polythioester-based, polysulfone-based, polysulfonamide-based, polyamide-based, polyimine-based, polyurea-based, polyaniline-based, polythiophene-based, polypyrrole-based, polyheterocyclic, polyether-based, polyphosphate-based, and polysilsesquioxane-based homopolymers; a derivative thereof; and a copolymer thereof or a derivative thereof.

9. The kit as set forth in claim 1, wherein the nitrite compound is at least one selected from the group consisting of sodium nitrite, potassium nitrite, magnesium nitrite, and calcium nitrite.

10. The kit as set forth in claim 1, wherein the proteolytic enzyme is at least one selected from the group consisting of pronase, protease A, protease N, dispase, neutral protease, glu-C, papain, trypsin, and pepsin.

11. The kit as set forth in claim 1, wherein the oxidizing agent is peroxidase (POD).

12. The kit as set forth in claim 1, wherein the fructosyl amino acid oxidase (FAOD) is fructosyl peptide oxidase (FPOX).

13. The kit as set forth in claim 1, wherein the color developing reagent is at least one selected from the group consisting of N-(carboxymethylaminocarbonyl)-4,4'-bis (dimethylamino)diphenylamine, 10-(carboxymethylaminocarbonyl)-3,7-bis(dimethylamino)phenothiazine sodium salt, 10-(N-methylcarbamoyl)-3,7-bis(dimethylamino)-1H-phenothiazine, N,N,N',N',N'',N''-hexa-3-sulfopropyl-4,4',4''-triaminotriphenylmethane, and ortho-phenylenediamine.

14. The kit as set forth in claim 1, wherein the kit for quantitative analysis of glycated hemoglobin (HbA1c) comprises a plurality of sample introduction units.

15. The kit as set forth in claim 14, wherein the first composition, second composition, third composition, and fourth composition are each independently fixed to a plurality of sample introduction units.

16. The kit as set forth in claim 1, wherein two ingredients selected from each composition are mixed with each other.

17. The kit as set forth in claim 16, wherein the combination of two ingredients is a combination of the second composition and the third composition.

18. The kit as set forth in claim 16, wherein the first composition, second composition, third composition, and fourth composition are fixed to the sample introduction unit in a dried state.

* * * * *